US005545645A

United States Patent [19]
Pascal et al.

[11] Patent Number: 5,545,645
[45] Date of Patent: Aug. 13, 1996

[54] HETEROCYCLIC DERIVATIVES IN THE TREATMENT OF ISCHAEMIA AND RELATED DISEASES

[75] Inventors: Jean-Claude Pascal, Cachan; Gary McCort; Dominique Blondet, both of Paris; Françoise Gellibert, Cachan, all of France

[73] Assignee: Syntex Pharmaceuticals, Limited, Maidenhead, England

[21] Appl. No.: 401,486

[22] Filed: Mar. 9, 1995

Related U.S. Application Data

[62] Division of Ser. No. 45,568, Apr. 9, 1993, Pat. No. 5,428,037.

[51] Int. Cl.⁶ .................. A61K 31/435; C07D 405/06; C07D 401/06; C07D 409/06
[52] U.S. Cl. .................. 514/326; 546/214; 546/213; 546/210; 546/208; 546/192; 546/193; 546/209; 546/194; 546/240; 546/236; 544/316; 544/319; 544/298; 544/333; 544/335; 544/242; 544/219; 544/180; 514/318; 514/317; 514/269; 514/274; 514/256; 514/241
[58] Field of Search .................. 546/214, 213; 514/326

[56] References Cited

U.S. PATENT DOCUMENTS

| | | | |
|---|---|---|---|
| 3,108,111 | 10/1963 | Stern et al. | 260/294.7 |
| 3,878,217 | 4/1975 | Carr et al. | 260/247.5 |
| 3,941,795 | 3/1976 | Carr et al. | 260/293.64 |
| 4,242,355 | 12/1980 | Nedelec et al. | 424/275 |
| 4,829,065 | 5/1989 | Pascal et al. | 514/255 |
| 4,918,073 | 4/1990 | Rüger et al. | 514/255 |
| 4,921,863 | 5/1990 | Sugimoto et al. | 514/319 |
| 5,043,447 | 8/1991 | Pascal et al. | 544/370 |
| 5,091,428 | 2/1992 | Pascal et al. | 544/309 |
| 5,252,736 | 10/1993 | Pascal et al. | 544/370 |

FOREIGN PATENT DOCUMENTS

| | | |
|---|---|---|
| 152799 | 8/1985 | European Pat. Off. |
| 229623 | 7/1987 | European Pat. Off. |
| 289227 | 11/1988 | European Pat. Off. |
| 63-141966 | 6/1988 | Japan . |
| 705979 | 3/1954 | United Kingdom . |
| 1443854 | 5/1976 | United Kingdom . |

OTHER PUBLICATIONS

G. B. Barlin et al., "Potential Antimalarials", *Austr. J. Chem.*, vol. 43, pp 1301–1307 (1990).

T. Iwamoto et al., "Effects of KB-2796, a New Calcium Antagonist, and other Diphenylpiperazines on [hu 3 H]Nitrendipine Binding", *Japan J. Pharmacol.* vol. 48, pp 241–247 (1988).

Katrinzky, *Handbook of Heterocyclic Chemistry*, p 425 (1985).

*Chemical Abstracts*, 11th Coll. Ind., vol. 96–105, Formulas, p 9892F (1982–86).

Primary Examiner—Mukund J. Shah
Assistant Examiner—King Lit Wong
Attorney, Agent, or Firm—Heller Ehrman White & McAuliffe

[57] ABSTRACT

Compounds of the formula:

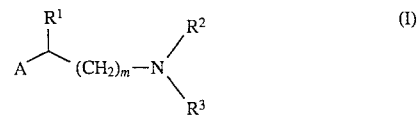

wherein:
 m is 0 or 1;
 $R^1$ is hydrogen, hydroxy, or lower alkyl;
 $R^2$ is hydrogen, or lower alkyl;
 $R^3$ is

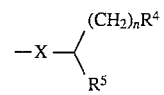

or $R^2$ and $R^3$ taken together with the nitrogen atom to which they are attached represent a group of the formula:

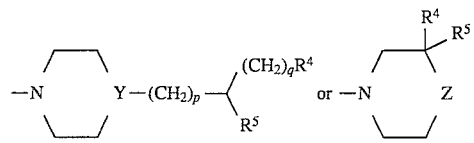

wherein:
 n is 0 or 1;
 p is 0, 1, 2 or 3;
 q is 0 or 1;
 $R^4$ is hydrogen, lower alkyl, cycloalkyl, or optionally substituted phenyl;
 $R^5$ is optionally substituted phenyl;
 X is $(CH_2)_p$, or 4-piperidin-1-yl;
 Y is CH, CH—O—, CH—S—, or nitrogen;
 Z is $CH_2$, NH, sulfur, or oxygen; and
 A is a substituted furanyl group.

10 Claims, No Drawings

HETEROCYCLIC DERIVATIVES IN THE TREATMENT OF ISCHAEMIA AND RELATED DISEASES

CROSS-REFERENCE TO RELATED APPLICATION

This application is a division of U.S. patent application Ser. No. 08/045,568, filed Apr. 9, 1993, now U.S. Pat. No. 5,428,037.

BACKGROUND OF THE INVENTION

1. Field of the Invention

This invention relates to substituted heterocyclic derivatives of Formula (I), the pharmaceutically acceptable salts thereof, methods of making these compounds, and pharmaceutical compositions containing them. The compounds of this invention are calcium and/or sodium channel antagonists, and are efficacious for the treatment of ischaemia and other disease states, and have protective activity against some of the deleterious effects resultant upon cerebral ischemia.

2. Background Information and Related Disclosures

The compounds of this invention are various amino heterocyclic derivatives. Compounds somewhat structurally related are described in U.S. Pat. Nos. 4,829,065, 5,043,447, 5,091,428, in GB Patent No. 1,434,854, and in JP 49093379.

SUMMARY OF THE INVENTION

A first aspect of the present invention relates to compounds of the Formula (I):

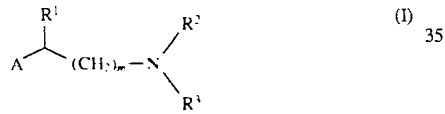

wherein:
m is 0 or 1;
$R^1$ is hydrogen, hydroxy, or lower alkyl;
$R^2$ is hydrogen, or lower alkyl;
$R^3$ is

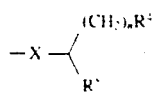

or $R^2$ and $R^3$ taken together with the nitrogen atom to which they are attached represent a group of the formula:

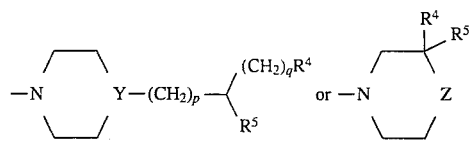

wherein:
n is 0 or 1;
p is 0, 1, 2 or 3;
q is 0 or 1;
$R^4$ is hydrogen, lower alkyl, cycloalkyl, or optionally substituted phenyl;
$R^5$ is optionally substituted phenyl;
X is $(CH_2)_p$, or 4-piperidin-1-yl;
Y is CH, CH—O—, CH—S—, or nitrogen;
Z is $CH_2$, NH, sulfur, or oxygen; and
A is chosen from the group consisting of:

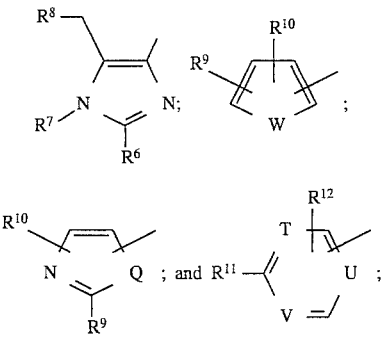

wherein:
Q is oxygen or sulfur;
$R^6$ is lower alkyl, or optionally substituted phenyl;
$R^7$ is hydrogen, lower alkyl or $CH(R^{13})OC(O)R^{14}$; in which
  $R^{13}$ is hydrogen or lower alkyl; and
  $R^{14}$ is lower alkyl, lower alkoxy, or lower alkoxyalkyl;
$R^8$ is hydrogen, lower alkyl, or optionally substituted phenyl;
$R^9$ is lower alkyl, or optionally substituted phenyl;
$R^{10}$ is hydrogen, or lower alkyl;
$R^{11}$ is lower alkyl or optionally substituted aryl;
$R^{12}$ is hydrogen, lower alkyl, lower alkoxy, halo, or trifluoromethyl;
T, U, and V are independently CH, or nitrogen; and
W is oxygen, sulfur, or $NR^{15}$;
wherein $R^{15}$ is hydrogen or lower alkyl;
with the proviso that $R^9$, $R^{10}$, $R^{12}$, and the sidechain cannot be attached to a hetero atom; and
with the proviso that when $R^7$ is hydrogen and $R^4$ is hydrogen or optionally substituted phenyl, q cannot be 0;

or a pharmaceutically acceptable acid addition salt or N-oxide thereof.

A second aspect of this invention relates to pharmaceutical compositions containing at least one compound of Formula (I) and one or more pharmaceutically acceptable excipients.

A third aspect of the invention relates to methods of treating mammals having a disease treated by direct neuronal protection or a disease treated by calcium channel inhibition, sodium channel inhibition, or inhibition of both calcium and sodium channels, including:

diseases treated by direct neuronal protection, such as ischaemia including focal and global ischaemia, cerebral ischaemia including ischaemia-induced neurodegeneration, perinatal asphyxia, spinal injuries, peripheral nerve ischaemia, peripheral nerve damage, head trauma, primary intracerebral hemorrhage, encephalopathy, epilepsy or epileptic psychotic symptoms, and neurological diseases such as Alzheimer's, Huntington's chorea, Parkinsons and dementias; and diseases treated by calcium channel inhibition, sodium channel inhibition, or inhibition of both calcium and sodium channels, including:

diseases treated by inhibiting cerebrovascular vasospasm and by cerebrovascular vasodilation, such as migraine, stroke, vasospasm due to subarachnoid hemorrhage, and cerebrovascular ischaemia induced by cocaine abuse;

diseases treated by inhibiting cellular oedema, such as cerebral oedema and hyponatraemic encephalopathy;

cardiovascular diseases, such as hypertension, angina, stable and unstable angina, Prinzmetal angina, arrhythmia, thrombosis, myocardial infarction, embolism, and congestive heart failure such as chronic or acute cardiac failure;

diseases characterized by ischaemia of lower legs due to peripheral vascular disease, including intermittent claudication;

diseases characterized by spasms of smooth muscle, including reversible airways obstruction, asthma, spasms of the ureter, spasms of the bladder, uterine cramps, and irritable bowel syndrome;

prevention of vasoconstriction and/or ischaemic tissue damage during a surgical procedure, such as bypass grafts, angiography, angioplasty, organ preservation during transplant, hypertensive crisis, or post-operative hypertension;

diseases treated by diuresis; and uraemic encephalopathy, by administering an effective amount of a compound of Formula (I), or a composition containing a compound of Formula (I), to the mammal.

A fourth aspect of the invention relates to methods for the preparation of the compounds of Formula (I).

DETAILED DESCRIPTION OF THE INVENTION

Definitions

As used herein:

"Alkyl" means a monoradical branched or unbranched saturated hydrocarbon chain containing 1 to 12 carbon atoms, such as methyl, ethyl, propyl, tert-butyl, n-hexyl, n-octyl, n-decyl, and the like, unless otherwise indicated.

"Lower alkyl" means a monoradical branched or unbranched saturated hydrocarbon chain containing 1 to 6 carbon atoms, such as methyl, ethyl, propyl, isopropyl, tert-butyl, butyl, n-hexyl, and the like, unless otherwise indicated.

"Cycloalkyl" means a saturated monovalent monocyclic hydrocarbon radical containing 3–8 carbon atoms, such as cyclopropyl, cyclobutyl, cyclopentyl, cyclohexyl, cycloheptyl and cyclooctyl, optionally substituted by lower alkyl as defined above.

"Lower alkoxy" means the group —O—R wherein R is lower alkyl is as defined above.

The term "halo" means fluoro, bromo, chloro or iodo, unless otherwise indicated.

The terms "inert organic solvent" or "inert solvent" mean a solvent inert under the conditions of the reaction being described in conjunction therewith [including, for example, benzene, toluene, acetonitrile, tetrahydrofuran ("THF"), dimethylformamide ("DMF"), chloroform ("CHCl$_3$"), methylene chloride (or dichloromethane or "CH$_2$Cl$_2$"), diethyl ether, ethyl acetate, acetone, methylethyl ketone, methanol, ethanol, propanol, isopropanol, tert-butanol, dioxane, pyridine, and the like]. Unless specified to the contrary, the solvents used in the reactions of the present invention are inert solvents.

The compounds of Formula (I) form acid addition salts by virtue of the presence of basic nitrogen atoms. "Pharmaceutically acceptable salt" means those salts which retain the biological effectiveness and properties of the compounds of Formula (I), and which are not biologically or otherwise undesirable. Acid addition salts may be formed with inorganic acids such as hydrochloric acid, hydrobromic acid, sulfuric acid, nitric acid, phosphoric acid and the like, and organic acids such as acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid, and the like.

The compounds of this invention may have one or more asymmetric centers (for example where R$^1$ is not hydrogen, or where q is 0 and R$^4$ is lower alkyl), and can be produced as racemic mixtures or as individual stereoisomers. The individual stereoisomers may be obtained by resolving a racemic or non-racemic mixture of an intermediate at some appropriate stage of the synthesis, or by resolution of a compound of Formula (I). It is understood that the individual stereoisomers as well as racemic and non-racemic mixtures of stereoisomers are encompassed within the scope of the present invention.

The term "aryl" means a monocyclic aromatic ring, and includes carbocycles and heterocycles. Examples of aryl groups are phenyl, thiophene, furan, imidazole, pyridine, pyrimidine, and the like.

"Optional" or "optionally" means that the subsequently described event or circumstance may or may not occur, and that the description includes instances where said event or circumstance occurs and instances in which it does not. For example, "optionally substituted phenyl" or "optionally substituted aryl" means that phenyl or aryl may or may not be substituted with a substituent selected from the group consisting of lower alkyl, lower alkoxy, hydroxy, nitro, trifluoromethyl and halo, and encompasses all possible isomeric phenyl radicals that are mono, di or trisubstituted.

The term "Y" is defined as CH, CH—O—, CH—S—, or nitrogen. This definition is intended to indicate that Y forms part of a ring having the structures:

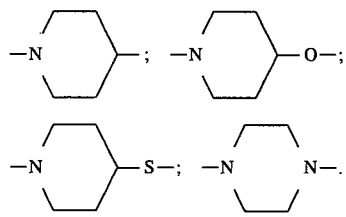

The term "mammal" includes humans and all domestic and wild mammals, including, without limitation, cattle, horses, swine, sheep, goats, dogs, cats, rabbits, and the like.

The term "treatment" as used herein covers any treatment of a disease in a mammal, particularly a human, and includes:

(i) preventing the disease from occurring in a subject which may be predisposed to the disease but has not yet been diagnosed as having it;

(ii) inhibiting the disease, i.e. arresting its development; or (iii) relieving the disease, i.e. causing regression of the disease.

The term "effective amount" means a dosage sufficient to provide treatment for the disease state being treated. This will vary depending on the patient, the disease and the treatment being effected.

The naming and numbering of the compounds of the present invention is illustrated below.

A compound of Formula (I) where A is an imidazole derivative is illustrated below as a compound of Formula (IA), and is numbered as follows:

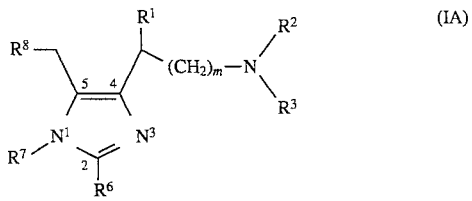
(IA)

A compound of Formula (IA) wherein $R^6$ is 4-trifluoromethylphenyl; $R^7$ is methyl; $R^8$ is hydrogen; m is 0; $R^1$ is hydrogen; and —$NR^2R^3$ represents a group of the formula:

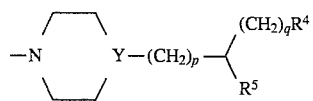

where p and q are 0; $R^4$ is hydrogen; $R^5$ is 2,3,4-trimethoxyphenyl; and Y is nitrogen; is named:

1-(2,3,4-trimethoxyphenyl)methyl-4-[(2-(4-trifluoromethylphenyl)- 1,5-dimethylimidazol-5-yl)methyl]piperazine.

A compound of Formula (IA) wherein $R^6$ is 4-trifluoromethylphenyl; $R^7$ is hydrogen; $R^1$ and $R^8$ are hydrogen; m is 0; and —$NR^2R^3$ represents a group of the formula:

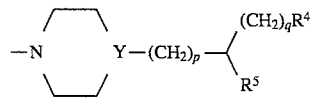

where p and q are 0; $R^4$ is isopropyl; $R^5$ is 2,3,4-trimethoxyphenyl; and Y is nitrogen; is named:

(±)-1-[(2,3,4-trimethoxyphenyl)-2-methylprop-1-yl]-4-[(2-(4-trifluoromethylphenyl)-4(5)-methyl-1H-imidazol-( 5)4-yl)methyl]piperazine.

A compound of Formula (I) where A is a furan, thiophene, or pyrrole derivative is illustrated below as a compound of Formula (IB), and is numbered as follows:

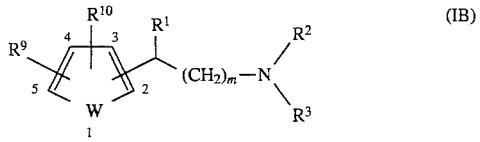
(IB)

A compound of Formula (IB) wherein $R^9$ is 5-phenyl; $R^{10}$ is 3-methyl; W is oxygen; and the sidechain is in the 2-position, in which m is 0; $R^1$ is hydrogen; and —$NR^2R^3$ represents a group of the formula:

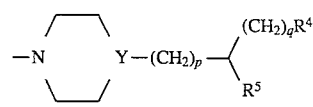

where p and q are 0; $R^4$ and $R^5$ are both phenyl; and Y is nitrogen; is named:

1-diphenylmethyl-4-[(3-methyl-5-phenylfuran-2-yl)methyl]piperazine.

A compound of Formula (I) where A is an oxazole or a thiazole derivative is illustrated below as a compound of Formula (IC), and is numbered as follows:

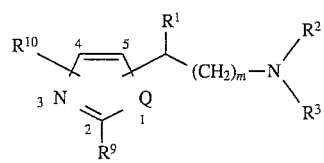
(IC)

A compound of Formula (IC) wherein Q is sulfur; $R^9$ is 4-trifluoromethylphenyl; $R^{10}$ is 4-methyl; m is 0; $R^1$ is hydrogen; and —$NR^2R^3$ represents a group of the formula:

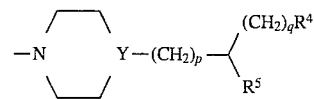

where p and q are 0; $R^4$ is hydrogen; $R^5$ is 2,3,4-trimethoxyphenyl; and Y is nitrogen; is named:

1-(2,3,4-trimethoxyphenyl)methyl-4-[(2-(4-trifluoromethylphenyl)- 4-methyl-1,3-thiazol-5-yl)methyl]piperazine.

A compound of Formula (I) where A is:

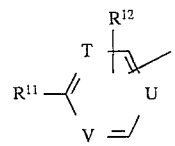

where T, U and V are all CH is illustrated below as a compound of Formula (IDA), and is numbered as follows:

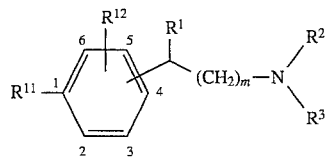
(IDA)

However, when $R^{11}$ is optionally substituted phenyl, the compounds are biphenyl derivatives, and are numbered accordingly:

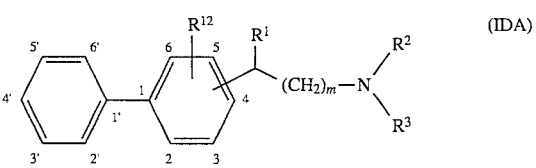
(IDA)

Thus, a compound of Formula (IDA) wherein $R^{11}$ is 4-methylphenyl; $R^{12}$ is 4-methyl; and the sidechain is in the 3-position; in which m is 0; $R^1$ is hydrogen; and —$NR^2R^3$ represents a group of the formula:

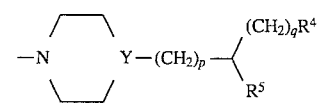

where p and q are 0; $R^4$ is hydrogen; $R^5$ is 2,3,4-trimethoxyphenyl; and Y is nitrogen; is named:

1-(2,3,4-trimethoxyphenyl)methyl-4-[4,4'-dimethylbiphenyl- 3-ylmethyl]piperazine.

A compound of Formula (I) where A is:

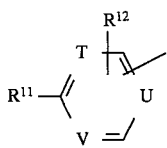

where T is nitrogen, V is CH or nitrogen, and U is CH is illustrated below as a compound of Formula (IDB), and is numbered as follows:

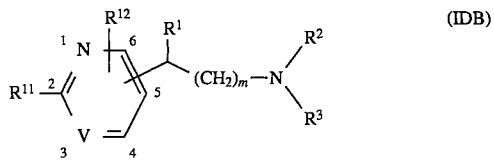

A compound of Formula (IDB) wherein V is nitrogen, $R^{11}$ is 4-trifluoromethylphenyl; $R^{12}$ is hydrogen, and the sidechain is in the 4-position; in which m is 0; $R^1$ is hydrogen; and —$NR^2R^3$ represents a group of the formula:

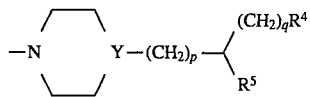

where p and q are 0; $R^4$ and $R^5$ are phenyl; and Y is nitrogen; is named:

1-diphenylmethyl-4-[2-(trifluoromethylphenyl)pyrimidin-4-yl)methyl]piperazine.

PREFERRED EMBODIMENTS

Among the family of compounds of the present invention, one preferred category includes the compounds of Formula (I) where A is:

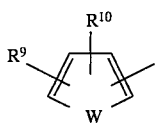

Within this category one preferred group includes the compounds where $R^2$ and $R^3$ taken together with the nitrogen atom to which they are attached represent a group of the formula:

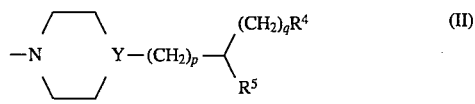

especially where m is 0, q is 0, and $R^1$ is hydrogen or lower alkyl, $R^9$ is optionally substituted phenyl and $R^{10}$ is lower alkyl. Within this group one preferred subgroup includes the compounds where p is 0, $R^1$ is hydrogen, and $R^4$ and $R^5$ are both phenyl, more especially where Y is nitrogen.

Another preferred group within this category includes the compounds where $R^2$ and $R^3$ taken together with the nitrogen atom to which they are attached represent a group of the formula:

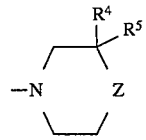

especially where Z is oxygen, and $R^4$ and $R^5$ are both phenyl.

Another preferred category includes the compounds of Formula (I) where A is:

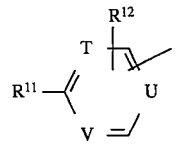

Within this category one preferred group includes the compounds where $R^2$ and $R^3$ taken together with the nitrogen atom to which they are attached represent a group illustrated as (II) above, especially where m is 0, q is 0, and $R^1$ is hydrogen or lower alkyl, $R^{11}$ is optionally substituted phenyl and $R^{12}$ is lower alkyl. Within this group one preferred subgroup includes the compounds where T, U, and V are all CH, especially where p is 0 and Y is nitrogen. Another preferred subgroup includes the compounds where T and V are nitrogen, and U is CH, especially where p is 0 and Y is nitrogen. Yet another preferred subgroup includes the compounds where U is CH, and T is CH when V is nitrogen, or T is nitrogen when V is CH, especially where p is 0 and Y is nitrogen.

A third preferred category includes the compounds of Formula (I) where A is:

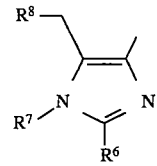

Within this category one preferred group includes the compounds where $R^2$ and $R^3$ taken together with the nitrogen atom to which they are attached represent a group illustrated as (II) above, especially where m, p and q are 0, and Y is nitrogen. Within this group one preferred subgroup includes the compounds where $R^7$ is lower alkyl, especially where $R^1$ and $R^8$ are hydrogen, and $R^6$ is optionally substituted phenyl, more especially where $R^4$ and $R^5$ are both optionally substituted phenyl, and where $R^4$ is hydrogen and $R^5$ is optionally substituted phenyl. Within this group another preferred subgroup includes the compounds where $R^7$ is hydrogen, especially where $R^1$ and $R^8$ are hydrogen, and $R^6$ is optionally substituted phenyl, more especially where $R^4$ is lower alkyl or cycloalkyl and $R^5$ is optionally substituted phenyl.

Another preferred subgroup within this group includes the compounds where m, p and q are 0, and $R^7$ is —$CH(R^{13})OC(O)R^{14}$, especially where $R^1$ is hydrogen, $R^6$ is optionally substituted phenyl, $R^8$ is hydrogen or lower alkyl, and Y is nitrogen, more especially where $R^{13}$ is hydrogen and $R^{14}$ is lower alkyl or lower alkoxy.

Another preferred group within this category includes the compounds where $R^2$ and $R^3$ taken together with the nitrogen atom to which they are attached represent a group illustrated as (III) above, especially where m is 0, Z is oxygen, and $R^4$ and $R^5$ are both optionally substituted phenyl. Within this group one preferred subgroup includes the compounds where $R^7$ is hydrogen, especially where $R^1$ and $R^8$ are hydrogen, and $R^6$ is optionally substituted phenyl.

A fourth preferred category includes the compounds of Formula (I) where A is:

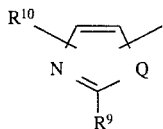

Within this category one preferred group includes the compounds where $R^2$ and $R^3$ taken together with the nitrogen atom to which they are attached represent a group illustrated as (II) above, especially where m and q are 0, and $R^1$ is hydrogen or lower alkyl, more especially where $R^9$ is optionally substituted phenyl and $R^{10}$ is lower alkyl. Within this group one preferred subgroup includes the compounds where p is 0, $R^1$ is hydrogen, and $R^4$ and $R^5$ are both optionally substituted phenyl, especially where Y is nitrogen.

At present, the preferred compounds are:

(±)-1-[(2,3,4-trimethoxyphenyl)eth-1-yl]-4-[(2-(4-trifluoromethylphenyl)-4( 5)-methyl-1H-imidazol-(5)4-yl)methyl]piperazine;

(±)-1-[(2,3,4-trimethoxyphenyl)-2-cyclopentyleth-1-yl]-4-[(2-(4-trifluoromethylphenyl)-4(5)-methyl-1H-imidazol-( 5)4-yl)methyl]piperazine; and (±)-1-[(2,3,4-trimethoxyphenyl)-2-methylprop-1-yl]- 4-[(2-(4-trifluoromethylphenyl)-4(5)-methyl-1H-imidazol-( 5)4-yl)methyl]piperazine.

PREPARATION OF COMPOUNDS OF FORMULA (I)

Preparation of Compounds of Formula (IA)

Compounds of Formula (I) where A is an imidazole derivative, illustrated as compounds of Formula (IA), may be prepared from 1,2,5-substituted (or 2,4(5)-substituted) imidazoles of Formula (6), the preparation of which is shown below in Reaction Scheme I.

REACTION SCHEME I

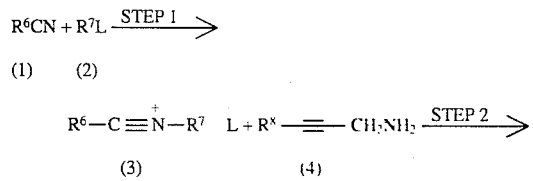

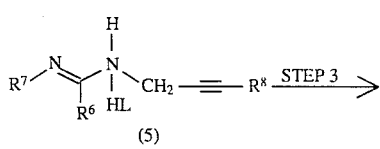

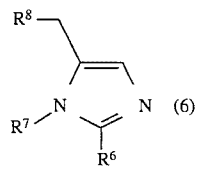

where L is —Cl or —SO$_3$CF$_3$, $R^7$ is lower alkyl, and $R^6$ and $R^8$ are as defined in the Summary of the Invention.

Step 1—Preparation of Compounds of Formula (3)

To prepare compounds of Formula (3), a nitrile of Formula (1) is reacted with about 1 to 1.5 molar equivalents, preferably about 1.05 molar equivalents, of a compound of Formula (2), $R^7L$. When L is Cl, 1 equivalent of ferric chloride is also added. The reaction is preferably carried out in the absence of solvent, at a temperature of about 50°–80° C., preferably at about 65° C., for about 1 to 8 hours, preferably about 4 hours. When the reaction is substantially complete, the next step is carried out without purification.

Step 2—Preparation of Compounds of Formula (5)

To prepare compounds of Formula (5), the compound of Formula (3) is reacted with about 1 to 1.5 molar equivalents, preferably about 1.05 molar equivalents, of a substituted acetylene of Formula (4). The reaction is carried out in an inert solvent, preferably acetonitrile, at a temperature of about 0°–40° C., preferably at about 25° C., for about 6 to 48 hours, preferably about 16 hours. When the reaction is substantially complete, the product of Formula (5) is separated conventionally, and reacted in the next step without purification.

Step 3—Preparation of Compounds of Formula (6)

To prepare compounds of Formula (6), a compound of Formula (5) is cyclized by heating in an inert solvent, (for example, benzene, toluene, xylene; preferably toluene), at a temperature of about from 80°–140° C., preferably at about 100° C., for about 1 to 8 hours, preferably about 3 hours. When the reaction is substantially complete, the product of Formula (6) is isolated and purified by conventional means, preferably crystallization.

Alternative Preparation of Compounds of Formula (6)

Preferably, the compounds of Formula (6) where $R^7$ is hydrogen are prepared as described in greater detail in copending application Serial No. ??/???,???, filed ?, entitled "Process For The Preparation Of 1,2,4-Substituted Imidazoles And Related Aminoalkylimidazole Derivatives," by McCort and Pascal (two of the present inventors, all of whom were subject to an obligation of assignment to the same entity at the time of the inventions), filed concurrently herewith, the disclosure of which is hereby incorporated by reference.

Preparation of Compounds of Formula (IA)

A. Preparation of Compounds of Formula (IA) where m is 0 and $R^1$ is Hydrogen

Compounds of Formula (IA) where m is o and $R^1$ is hydrogen are prepared from the imidazoles of Formula (6), as shown in Reaction Scheme IIA.

REACTION SCHEME IIA

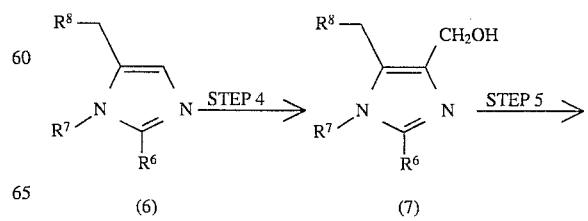

REACTION SCHEME IIA -continued

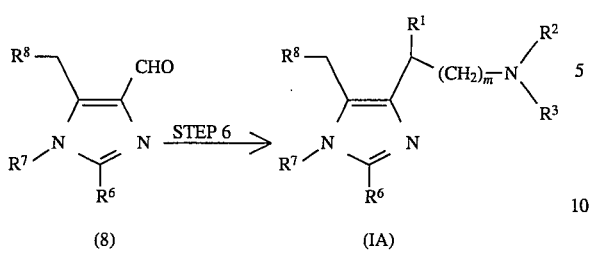

(8)    (IA)

where m is 0, $R^1$ is hydrogen, $R^7$ is hydrogen or lower alkyl, and $R^2$, $R^3$, $R^6$, and $R^8$ are as defined in the Summary of the Invention.

Step 4—Preparation of Compounds of Formula (7)

To prepare compounds of Formula (7), an imidazole of Formula (6) is reacted with an excess of formaldehyde in the presence of an organic acid and its sodium salt, preferably acetic acid and sodium acetate, at a temperature of about 80°–140° C., preferably at about 120° C., for about 10 to 48 hours, preferably about 24 hours. When the reaction is substantially complete, the product of Formula (7) is isolated and purified by conventional means, preferably chromatography.

Step 5—Preparation of Compounds of Formula (8)

To prepare compounds of Formula (8), a compound of Formula (7) is reacted with an excess of an oxidizing agent (for example, manganese dioxide, ammonium cerium(IV) nitrate, preferably manganese dioxide). The reaction is carried out in an inert solvent, preferably chloroform, at a temperature of about 50°–80° C., preferably at about 60° C., for about 6 to 48 hours, preferably about 24 hours. When the reaction is substantially complete, the product of Formula (8) is isolated and purified by conventional means.

Step 6—Preparation of Compounds of Formula (IA) where m is 0 and $R^1$ is Hydrogen To prepare compounds of Formula (IA), an amine of formula $HNR^2R^3$ is reacted with about 1 to 3 molar equivalents, preferably about 1.2 molar equivalents of a compound of Formula (8) in the presence of a titanium(IV) catalyst (for example titanium tetrachloride, titanium(IV) ethoxide, titanium(IV)isopropoxide, preferably titanium(IV)isopropoxide). The reaction is carried out in a protic solvent (for example methanol, ethanol, propanol, preferably ethanol), at a temperature of about 0°–40° C., preferably at about 25° C., for about 10 minutes to 4 hours, preferably about 1 hour. To the reaction mixture is then added a reducing agent (for example sodium borohydride, sodium cyanoborohydride, preferably sodium cyanoborohydride), and the reaction continued for about 10 minutes to 4 hours, preferably about 1 hour. When the reaction is substantially complete, the product of Formula (IA) is isolated and purified by conventional means, preferably flash chromatography followed by conversion to an acid salt, preferably a hydrochloride salt.

B. Alternative Preparation of Compounds of Formula (IA) where m is 0, and $R^1$ and $R^7$ are Hydrogen Compounds of Formula (IA) where m is 0, and $R^1$ and $R^7$ are hydrogen may also be prepared from the imidazoles of Formula (6), as shown in Reaction Scheme IIB. This is the preferred procedure for preparing compounds of Formula (IA) where $R^7$ is hydrogen.

REACTION SCHEME IIB

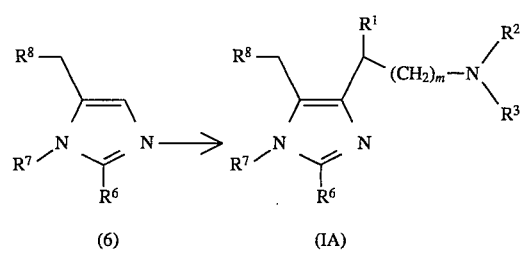

(6)    (IA)

where m is 0, and $R^1$ and $R^7$ are hydrogen, and $R^2$, $R^3$, $R^6$, and $R^8$ are as defined in the Summary of the Invention.

Preparation of a Compound of Formula (IA)

The compound of Formula (6), prepared as shown above, is reacted with about 1 to 1.2 molar equivalents, preferably about 1 molar equivalent, of an amine of Formula $HNR^2R^3$, and about 2 to 10 molar equivalents, preferably about 6 molar equivalents, of formaldehyde, preferably 37% aqueous formaldehyde. The reaction is carried out in an inert solvent (for example acetone, methanol, ethanol, n-propanol, water, preferably ethanol), at a temperature of about 50°–100° C., preferably at about reflux temperature, for about 30 minutes to 6 hours, preferably about 1 hour. The product of Formula (IA) is isolated by conventional means, preferably by conversion to an acid addition salt followed by crystallization.

Alternatively, the compound of Formula (6) is reacted with formaldehyde and an acid addition salt of an amine of Formula $HNR^2R^3$ in the proportions shown above. In this manner, the product of Formula (IA) is obtained as an acid addition salt directly, which is preferably purified by crystallization.

C. Preparation of Compounds of Formula (IA) where m is 2 and $R^1$ is Hydrogen

Compounds of Formula (IA) where m is 2 and $R^1$ is hydrogen are prepared from the 4-formylimidazoles of Formula (8), as shown in Reaction Scheme IIC.

REACTION SCHEME IIC

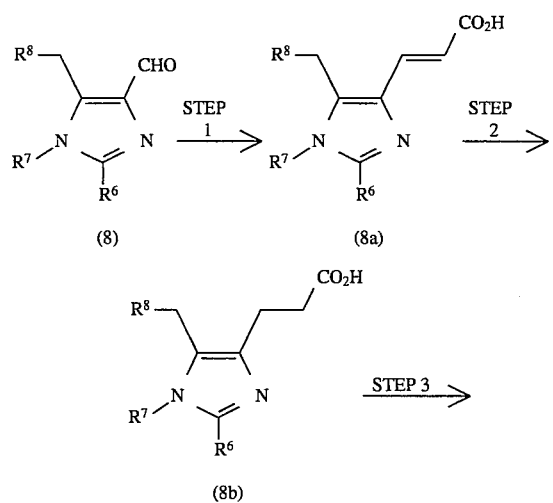

-continued
REACTION SCHEME IIC

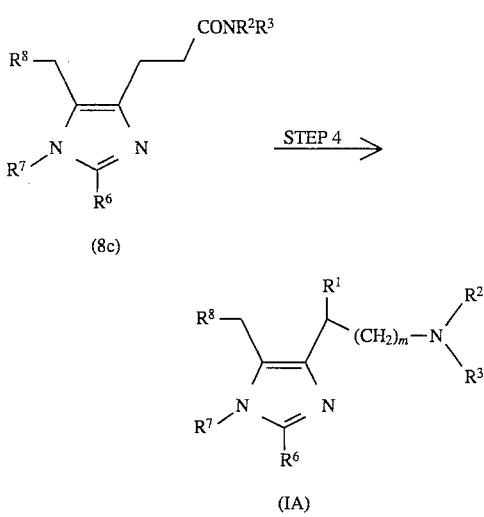

where m is 2, $R^1$ is hydrogen, $R^7$ is hydrogen or lower alkyl, and $R^2$, $R^3$, $R^6$, and $R^8$ are as defined in the Summary of the Invention.

Step 1—Preparation of Compounds of Formula (8a)

To prepare compounds of Formula (8a), an imidazole of Formula (8) is reacted with about 2 equivalents of malonic acid in the presence of piperidine, and pyridine as a solvent. The reaction is carried out at reflux for about 2 hours, and is then allowed to stand at room temperature for about 12 hours. When the reaction is substantially complete, the product of Formula (8a) is isolated and purified by conventional means.

Step 2—Preparation of Compounds of Formula (8b)

To prepare compounds of Formula (8b), a compound of Formula (8a) is hydrogenated in an inert solvent, preferably ethanol, under about 1–5 atmospheres of hydrogen, preferably about 1 atmosphere, in the presence of a noble metal catalyst (for example platinum on carbon, platinum oxide, palladium on carbon, preferably palladium on carbon), at a temperature of about 0°–40° C., preferably at about 25° C., for about 24–72 hours, preferably about 48 hours. When the reaction is substantially complete, the product of Formula (8b) is isolated and purified by conventional means.

Step 3—Preparation of Compounds of Formula (8c)

To prepare compounds of Formula (8c), a compound of Formula (8b) is reacted with about 1.5 equivalents of an amine of formula $HNR^2R^3$ in the presence of about 1.5 equivalents of dicyclohexylcarbodiimide, in an inert solvent, preferably methylene chloride, at a temperature of about reflux temperature, for about 1–8 hours, preferably about 2 hours. When the reaction is substantially complete, the product of Formula (8c) is isolated and purified by conventional means, preferably chromatography.

Step 4—Preparation of Compounds of Formula (IA) where m is 2 and $R^1$ is Hydrogen To prepare compounds of Formula (IA), a compound of Formula (8c) is reacted with about 1 to 6 molar equivalents, preferably about 4 molar equivalents, of a suitable reducing agent, preferably lithium aluminum hydride. The reaction is carried out in an ethereal solvent, preferably tetrahydrofuran, at a temperature of about 0°–40° C., preferably at about 25° C., for about 12–48 hours, preferably about 16 hours. When the reaction is substantially complete, the imidazole of Formula (IA) is isolated and purified by conventional means, preferably flash chromatography.

D. Preparation of Optically Active Compounds of Formula (IA)

Compounds of Formula (IA) where $R^4$ is lower alkyl have an asymmetric center, and thus can be separated into optically active enantiomers. The enantiomers of a compound of Formula (IA) may be obtained, for example, by separation of a racemic compound of Formula (IA) on a preparative HPLC column (such as a chirocel column, eluting with n-heptane/isopropanol/diethylamine 96/2/0.5).

Alternatively, the enantiomers of a compound of Formula (IA) may be obtained by asymmetric synthesis as follows: a chiral α-alkylbenzylamine is prepared from an appropriately substituted arylalkyl ketone (for example, 2,3,4-trimethoxy-acetophenone) by the method disclosed in *Tetrahedron Letters*, Vol. 30, No. 3, pp 317–320 (1989). The chiral amine is converted to the corresponding 1,4-disubstituted piperazine-2,6-dione by cyclization with benzyliminoacetic acid in the presence of carbonyldiimidazole in a suitable solvent, preferably tetrahydrofuran. The imide thus produced is reduced using lithium aluminum hydride, and the resultant benzylpiperazine is debenzylated by transfer hydrogenation in methanol, using ammonium formate and 10% palladium on charcoal. The chiral α-alkylbenzylamine is then converted to a chiral compound of Formula (IA) as shown above, i.e. Mannich reaction, reductive amination, etc.

Preparation of Compounds of Formula (IA) where $R^7$ is $R^{14}C(O)OCH(R^{13})$—

Compounds of Formula (IA) where $R^7$ is $R^{14}C(O)OCH(R^{13})$— are prepared from compounds of Formula (IA) where $R^7$ is hydrogen, designated as Formula (IA'), as shown in Reaction Scheme IID.

REACTION SCHEME IID

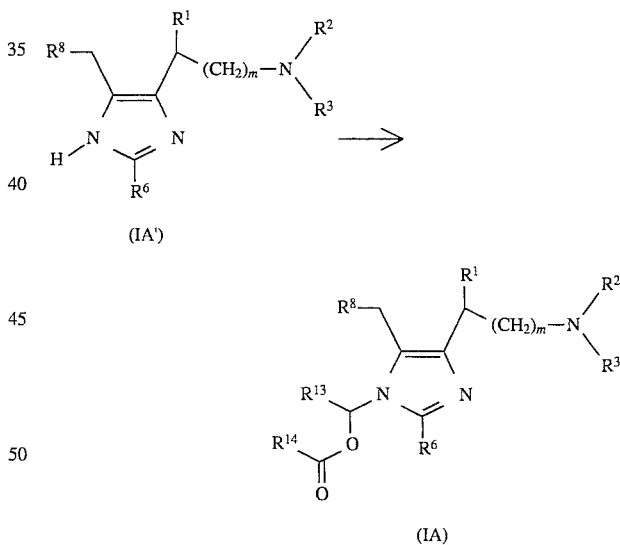

where m, $R^1$, $R^2$, $R^3$, $R^6$, $R^8$, $R^{13}$, and $R^{14}$ are as defined in the Summary of the Invention.

Starting Materials

The preparation of compounds of Formula (IA') is described in U.S. Pat. Nos. 4,829,065 and 5,043,447, the disclosure of which is hereby incorporated by reference. Alternatively, the compounds of Formula (IA') may be prepared as shown in Reaction Schemes I and II above, where $R^7$ represents hydrogen. Preferably, the compounds of Formula (IA') are prepared as described in copending application Serial No. ??/???,???, filed ?, entitled "Process For The Preparation Of 1,2,4-Substituted Imidazoles And Related Aminoalkylimidazole Derivatives," filed concurrently herewith, the disclosure of which is hereby incorporated by reference.

Preparation of Compounds of Formula (IA) where $R^7$ is $R^{14}C(O)OCH(R^{13})$—

To prepare compounds of Formula (IA) where $R^7$ is $R^{14}C(O)OCH(R^{13})$—, a compound of Formula (IA') is first reacted with about 1 to 1.5 molar equivalents, preferably about 1.1 molar equivalents, of a strong base (such as potassium hydride, lithium hydride, butyl lithium, sodium hydride, preferable sodium hydride). The resulting salt is reacted with about 0.9 to 1.5 molar equivalents, preferably about 1 molar equivalent, of an ester of formula $ClCH(R^{13})OC(O)R^{14}$, where $R^{13}$ and $R^{14}$ are as defined in the Summary of the Invention. The reaction is carried out in an ethereal solvent (for example ether, dimethoxymethane, tetrahydrofuran, preferably tetrahydrofuran), at a temperature of about 0°–40° C., preferably at about 25° C., for about 4–48 hours, preferably about 16 hours. When the reaction is substantially complete, the product of Formula (IA) where $R^7$ is $R^{14}C(O)OC(R^{13})H$— is isolated and purified by conventional means, preferably flash chromatography followed by conversion to an acid salt, preferably a methanesulfonic acid salt.

Preparation of Compounds of Formula (IB)

Compounds of Formula (I) where A is a furan, thiophene, or pyrrole derivative, illustrated as compounds of Formula (IB), may be prepared from compounds of Formulae (9) or (10), as shown below in Reaction Schemes IIIA and IIIB.

A. Preparation of Compounds of Formula (IB) where m is 0 and $R^1$ is Hydrogen

REACTION SCHEME IIIA

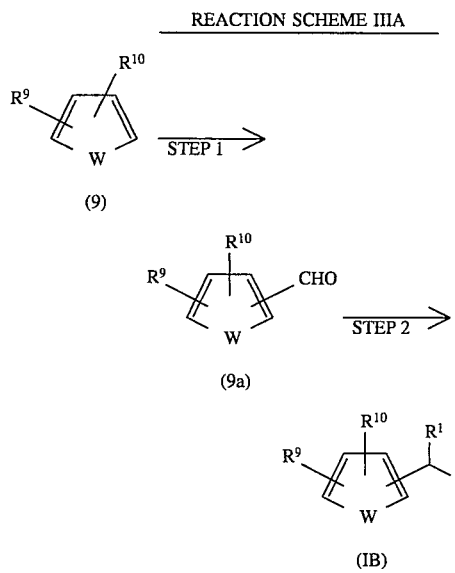

where m is 0, $R^1$ is hydrogen, and $R^2$, $R^3$, $R^9$, $R^{10}$, and W are as defined in the Summary of the Invention.

Starting Materials

The compounds of Formula (9) are commercially available, or can be made by the methods disclosed in Utimato et al., *Tet. Lett.*, Vol. 22, pp 4277–8 (1981), Evans et al., *J.O.C.*, Vol. 39, pp 914–7 (1974), *Zh. Ob. Khimi*, Vol. 43, p2749 (1973), Mukaiyama et al., *Chem. Lett.*, pp 527, Compaigne et al., *J. Het. Chem.*, Vol. 25, p 367 (1988), *J.O.C.*, Vol. 25, p 392 (1960), and Shridhar et al., *Synthesis*, pp 1061–2 (1982).

Step 1—Preparation of Compounds of Formula (9a)

To prepare compounds of Formula (9a), first about 1 molar equivalent of phosphorus oxychloride is reacted with about 1 molar equivalent of N,N-dimethylformamide, preferably in the absence of solvent, at a temperature of about −10° to 10° C., preferably at about 0° C., for about 10 minutes to 2 hours, preferably about 30 minutes. About 1 molar equivalent of a compound of Formula (9) dissolved in an inert solvent (such as dichloromethane, chloroform, dichloroethane, preferably dichloroethane) is then added. The reaction is carried out at a temperature of about 0° to 40° C., preferably at about 25° C., for about 30 minutes to 5 hours, preferably about 1½ hours. When the reaction is substantially complete, the formyl compound of Formula (9a) is isolated and purified by conventional means, preferably flash chromatography.

Step 2—Preparation of compounds of Formula (IB) where m is 0 and $R^1$ is Hydrogen To prepare compounds of Formula (IB) where m is 0 and $R^1$ is hydrogen, a compound of Formula (9a) is reacted with an amine of formula $HNR^2R^3$ in the presence of a titanium(IV) catalyst, followed by reduction of the intermediate imine, as described for the conversion of compounds of Formula (8) to compounds of Formula (IA) in Reaction Scheme II, Step 6. Such a reaction is also described in Mattson, *J.O.C.*, Vol. 55, p2552 (1990).

Alternative Step 2—Preparation of Compounds of Formula (IB) where m is 0 and $R^1$ is Lower Alkyl To prepare compounds of Formula (IB) where m is 0 and $R^1$ is lower alkyl, a compound of Formula (9a) is first reacted with an amine of formula $HNR^2R^3$ in the presence of a titanium(IV) catalyst, as shown above in Reaction Scheme IIIA, but the intermediate imine is then reacted with a Grignard reagent of formula $R^1MgBr$ (in place of the reducing agent), by means well known in the art. When the reaction is substantially complete, the product of Formula (IB) where m is 0 and $R^1$ is lower alkyl is isolated and purified by conventional means, preferably flash chromatography followed by conversion to an acid salt, preferably a hydrochloride salt.

B. Preparation of Compounds of Formula (IB) where m is 1 and $R^1$ is Hydroxy

REACTION SCHEME IIIB

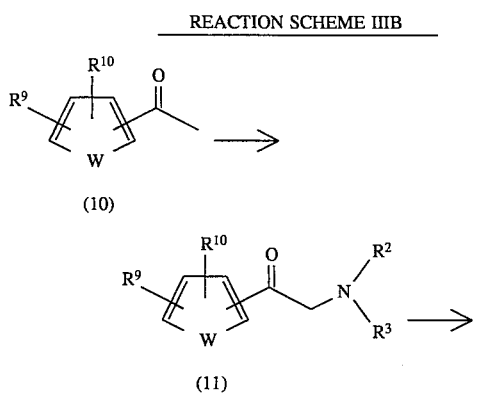

-continued
REACTION SCHEME IIIB

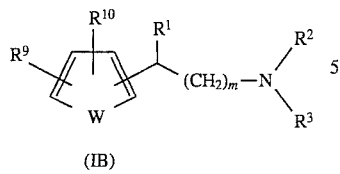

(IB)

where m is 1, $R^1$ is hydroxy, and $R^2$, $R^3$, $R^9$, $R^{10}$, and W are as defined in the Summary of the Invention.

Starting Materials

The compounds of Formula (10) are commercially available, or can be made by the methods disclosed in *J.A.C.S.* vol. 75, 5956 (1953), *Tetrahedron*, Vol. 44, 3343 (1988), and *Ber.*, 616 (1964).

Preparation of Compounds of Formula (IB) where m is 1 and $R^1$ is Hydroxy

To prepare compounds of Formula (IB) where m is 1 and $R^1$ is hydroxy, a compound of Formula (10) is first reacted with a halogenating agent (for example, bromine, pyrrolidine hydrotribromide, preferably pyrrolidine hydrotribromide). The reaction is carried out in an ethereal solvent (for example ether, dimethoxymethane, tetrahydrofuran, preferably tetrahydrofuran), at a temperature of about 0°–40° C., preferably at about 25° C., for about 4–48 hours, preferably about 16 hours. When the reaction is substantially complete, the product (an acyl bromide) is isolated and reacted with about 1 to 3 molar equivalents, preferably about 1.1 molar equivalents, of an amine of formula $HNR^2R^3$ in the presence of excess base, preferably potassium carbonate. The reaction is carried out in a protic solvent (for example methanol, ethanol, propanol, preferably propanol), at a temperature of about 40°–100° C., preferably at about reflux temperature, for about 30 minutes to 4 hours, preferably about 2 hours. When the reaction is substantially complete, the product of Formula (11) is isolated and purified by conventional means, preferably flash chromatography.

The compound of Formula (11) is then reduced conventionally, preferably with sodium borohydride in methanol, to give the compound of Formula (IB) where m is 1 and $R^1$ is hydroxy.

Preparation of Compounds of Formula (IC)

Compounds of Formula (I) where A is an oxazole or thiazole derivative, illustrated as compounds of Formula (IC), may be prepared from compounds of Formula (12), as shown below in Reaction Scheme IV.

REACTION SCHEME IV

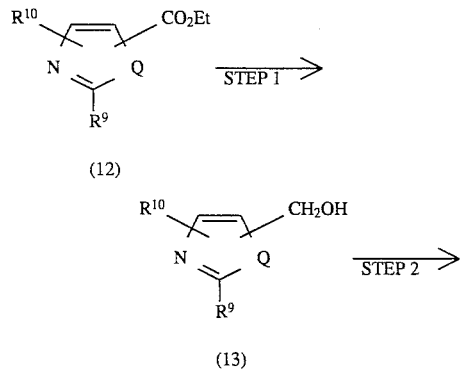

-continued
REACTION SCHEME IV

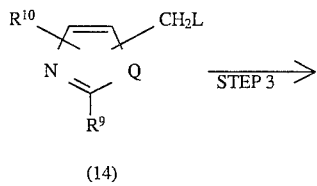

(14)

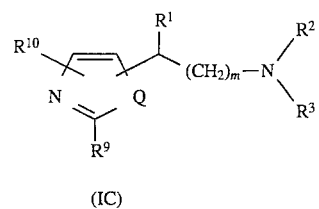

(IC)

where L is chlorine or bromine, m is 0, $R^1$ is hydrogen, and $R^2$, $R^3$, $R^9$, $R^{10}$, and Q are as defined in the Summary of the Invention.

Starting Materials

The compounds of Formula (12) are commercially available, or can be made by the methods disclosed in Tarzia, *Eur. J. Med. Chem.*, Vol. 3, p 263 (1976), in European Patent Application EP 0220573, or by means well known in the art.

Step 1—Preparation of Compounds of Formula (13)

To prepare compounds of Formula (13), a compound of Formula (12) is reacted with about 1 to 3 molar equivalents, preferably about 1.5 molar equivalents, of a suitable reducing agent (for example borane, triethyloxonium fluoroborate followed by sodium borohydride, sodium borohydride in the presence of a carboxylic acid, or preferably lithium aluminum hydride). The reaction is carried out in an ethereal solvent (for example ether, dimethoxymethane, tetrahydrofuran, preferably a mixture of ether and tetrahydrofuran), at a temperature of about 0°–40° C., preferably at about 25° C., for about 30 minutes to 8 hours, preferably about 1½ hours. When the reaction is substantially complete, the alcohol of Formula (13) is isolated and purified by conventional means, preferably flash chromatography.

Step 2—Preparation of Compounds of Formula (14)

To prepare compounds of Formula (14), the compound of Formula (13) is reacted with about 1 to 4 molar equivalents, preferably about 2 molar equivalents, of thionyl chloride or thionyl bromide. The reaction is carried out in an inert solvent, preferably dichloromethane, at a temperature of about 0°–40° C., preferably at about 25° C., for about 20 minutes to 6 hours, preferably about 1 hour. When the reaction is substantially complete, the product of Formula (14) is separated conventionally, and reacted in the next step without purification.

Step 3—Preparation of Compounds of Formula (IC)

To prepare compounds of Formula (IC), a compound of Formula (14) is reacted with 1 to 3 molar equivalents, preferably about 1 molar equivalents, of an amine of formula $HNR^2R^3$ in the presence of excess base, preferably potassium carbonate. The reaction is carried out in an inert solvent preferably acetonitrile, at a temperature of about 40°–100° C., preferably at about reflux temperature, for about 30 minutes to 4 hours, preferably about 2 hours. When the reaction is substantially complete, the product of Formula (IC) is isolated and purified by conventional means, preferably flash chromatography, followed by crystallization of an acid salt, preferably a hydrochloride salt.

Preparation of Compounds of Formula (ID)

Preparation of Compounds of Formula (IDA)
Compounds of Formula (I) where A is:

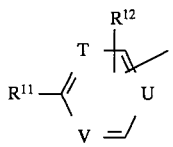

in which T, U and V are CH, are illustrated as compounds of Formula (IDA). They may be prepared from compounds of Formula (19), the preparation of which is shown below in Reaction Scheme V.

REACTION SCHEME V

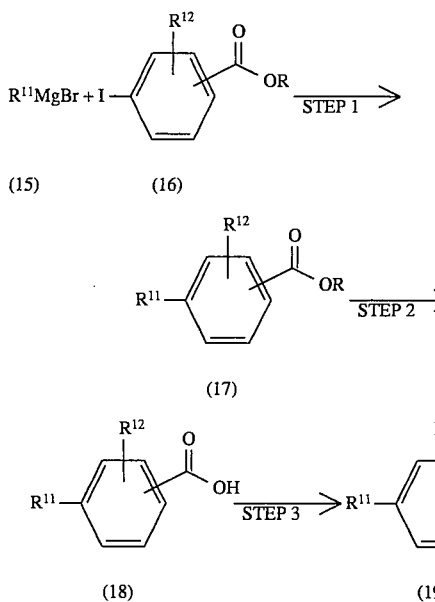

where R is lower alkyl, and $R^2$, $R^3$, $R^{11}$, and $R^{12}$, are as defined in the Summary of the Invention.

Starting Materials

The compounds of Formulae (15) and (16) are commercially available from Aldrich, for example, or can be made by the methods disclosed in *Tet. Lett.*, Vol. 29(11), pp 1293–1294 (1988) and *J. Med. Chem.*, Vol. 32, pp 105 118 (1989), or can be made for example as shown in Reaction Scheme VA below.

REACTION SCHEME VA

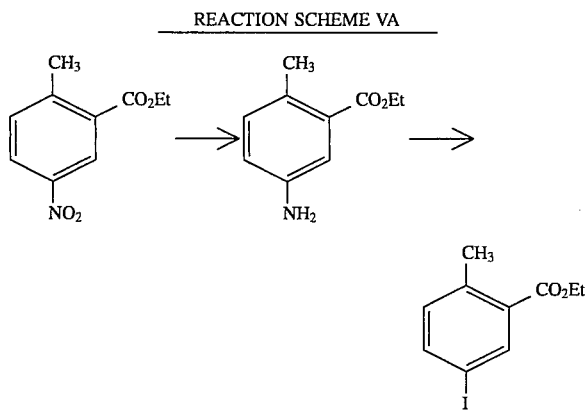

The nitro ester is reduced to the amino ester by means well known in the art, for example hydrogenation using palladium on carbon as a catalyst. The amine is then converted to the iodo compound by means well known in the art, for example diazotisation of the amine with sodium nitrite, followed by treatment with potassium iodide.

Step 1—Preparation of Compounds of Formula (17)

To prepare compounds of Formula (17), a compound of Formula (16) is reacted with about 1 to 3 molar equivalents, preferably about 1.5 molar equivalents, of a compound of Formula (15) in the presence of a Grignard reaction catalyst (for example about 0.05 molar equivalents of nickel(II) chloride, [1,3-bis(diphenylphosphino)propane]nickel(II) chloride, or reduced palladium prepared in situ from [1,3-bis(triphenylphosphino)palladium(II) chloride and diisobutylaluminum hydride, preferably nickel(II) chloride). The reaction is carried out in an ethereal solvent (for example ether, dimethoxymethane, tetrahydrofuran, preferably tetrahydrofuran), at a temperature of about 0°–40° C., preferably at about 25° C., for about 4–48 hours, preferably about 16 hours. When the reaction is substantially complete, the ester of Formula (17) is isolated and purified by conventional means, preferably flash chromatography.

Step 2—Preparation of Compounds of Formula (18)

To prepare compounds of Formula (18), a compound of Formula (17) is hydrolysed conventionally, for example by heating with a strong base in a protic solvent, for example sodium hydroxide in aqueous ethanol, and isolating and purifying the acid of Formula (18) by conventional means.

Step 3—Preparation of Compounds of Formula (19)

To prepare compounds of Formula (19), a compound of Formula (18) is first reacted with about 1 to 1.5 molar equivalents, preferably about 1.2 molar equivalents, of a halogenating agent (for example, phosphorus oxychloride, phosphorus trichloride, phosphorus pentachloride, thionyl chloride, preferably thionyl chloride). The reaction is carried out in a mixture of an inert solvent (for example chloroform, ethyl acetate, methylene chloride, preferably methylene chloride) and dimethylformamide, at a temperature of about 40°–80° C., preferably at about reflux temperature, until the reaction is complete. This mixture is then reacted with about 1 to 3 molar equivalents, preferably about 1.5 molar equivalents, of an amine of formula $HNR^2R^3$. The reaction is carried out at a temperature of about 0°–40° C., preferably at about 25° C., for about 4–48 hours, preferably about 16 hours. When the reaction is substantially complete, the amide of Formula (19) is isolated and purified by conventional means, preferably flash chromatography.

Preparation of Compounds of Formula (IDA)

Compounds of Formula (ID), in which T, U and V are CH, are prepared from the derivatives of Formula (19), as shown in Reaction Scheme VI.

REACTION SCHEME VI

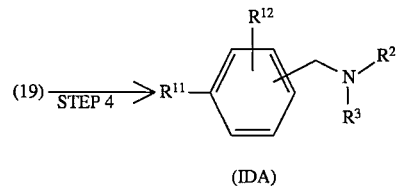

where $R^2$, $R^3$, $R^{11}$ and $R^{12}$ are as defined in the Summary of the Invention.

Step 4—Preparation of Compounds of Formula (IDA) where m is 0 and $R^1$ is Hydrogen To prepare compounds of Formula (IDA) where m is 0 and $R^1$ is hydrogen, a compound of Formula (19) is reacted with about 1 to 3 molar equivalents, preferably about 1.5 molar equivalents, of a suitable reducing agent (for example borane, triethyloxonium fluoroborate followed by sodium borohydride, or preferably lithium aluminum hydride). The reaction is carried out in an ethereal solvent (for example ether, dimethoxymethane, tetrahydrofuran, preferably a mixture of ether and tetrahydrofuran), at a temperature of about 0°–40° C., preferably at about 25° C., for about 30 minutes to 8 hours, preferably about 1½ hours. When the reaction is substantially complete, the amine of Formula (IDA) is isolated and purified by conventional means, preferably flash chromatography followed by conversion to an acid salt, preferably a hydrochloride salt.

Alternative Preparation of Compounds of Formula (ID)

Alternatively, compounds of Formula (IDA) where m is 0 and $R^1$ is hydrogen may be prepared from the compounds of Formula (17), as shown in Reaction Scheme VII.

REACTION SCHEME VII

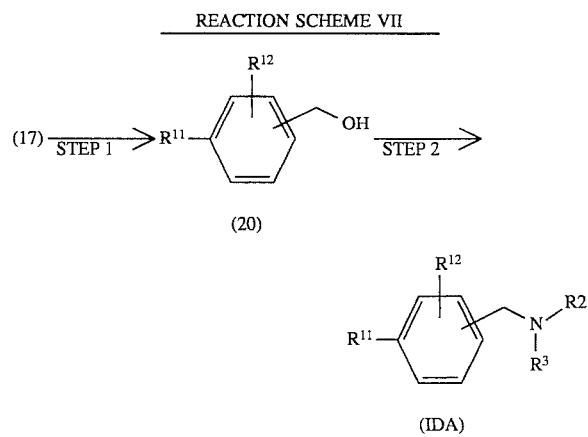

where $R^2$, $R^3$, $R^{11}$ and $R^{12}$ are as defined in the Summary of the Invention.

Step 1—Preparation of Compounds of Formula (20)

Compounds of Formula (20) are prepared from compounds of Formula (17) in the same manner as shown for the conversion of (12) to (13), in Reaction Scheme IV, Step 1.

Step 2—Preparation of Compounds of Formula (IDA) where m is 0 and $R^1$ is Hydrogen To prepare compounds of Formula (IDA) where m is 0 and $R^1$ is hydrogen, the hydroxy group of the —CH$_2$OH moiety of a compound of Formula (20) is first converted into a leaving group, for example by conversion to a halo group by means well known in the art, or preferably by reacting with about 1 to 1.5 molar equivalents, preferably about 1.2 molar equivalents, of a sulfonylating agent (for example, p-toluenesulfonyl chloride, or preferably methanesulfonyl chloride) in an inert organic solvent (such as benzene, toluene, ethyl acetate, acetonitrile, tetrahydrofuran, diethyl ether, chloroform, or dichloromethane, preferably dichloromethane) containing from 1–10 molar equivalents, preferably about 1.3 molar equivalents, of an inorganic base (such as sodium carbonate, potassium bicarbonate or the like), or preferably a tertiary organic base (such as pyridine, N-methylpiperidine and the like, preferably triethylamine), at a temperature of about 0°–40° C., preferably at about 25° C., for about 2 to 24 hours, preferably about 16 hours. The product is isolated and purified by conventional means, and then reacted with about 1 to 3 molar equivalents, preferably about 1.2 molar equivalents, of an amine of formula HNR$^2$R$^3$. The reaction is carried out in an inert solvent as defined above, preferably acetonitrile, in the presence of about 1–3 molar equivalents, preferably about 1.2 molar equivalents, of an organic base or inorganic base as defined above, preferably potassium bicarbonate, at a temperature of about 20°–100° C., preferably at about 60° C., for about 1–8 hours, preferably about 3 hours. When the reaction is substantially complete, the compound of Formula (IDA) is isolated and purified by conventional means, preferably flash chromatography followed by conversion to an acid salt, preferably a hydrochloride salt.

Preparation of Compounds of Formula (IDB)

Compounds of Formula (I) where A is:

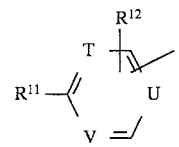

in which at least one of T, U and V is nitrogen, are illustrated as compounds of Formula (IDB).

1. The compounds of Formula (IDB) where T and V are nitrogen and U is CH may be prepared as shown below in Reaction Scheme VIII.

REACTION SCHEME VIII

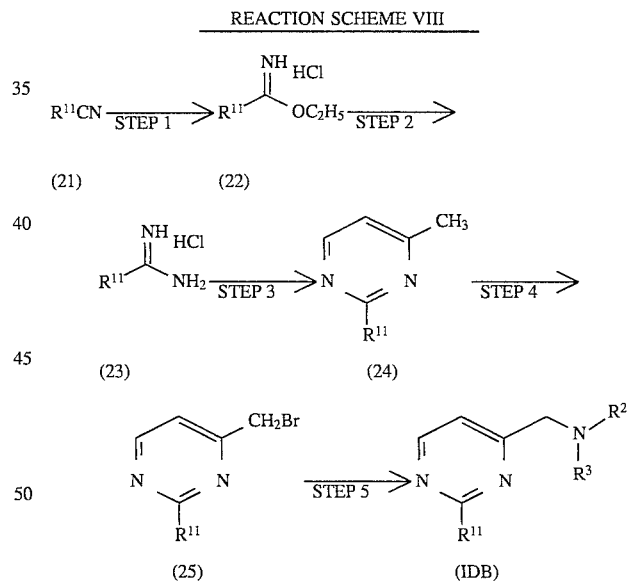

where $R^2$, $R^3$, and $R^{11}$ are as defined in the Summary of the Invention.

Step 1—Preparation of Compounds of Formula (22)

A nitrile of Formula (21) is converted to an imino ether of Formula (22) by means well known in the art, for example by treatment with an appropriate alcohol, preferably ethanol, in the presence of a strong acid, preferably anhydrous hydrochloric acid. The product is isolated and purified by conventional means.

Step 2—Preparation of Compounds of Formula (23)

The imino ether of Formula (22) is converted to an amidine of Formula (23) by means well known in the art, preferably by treatment with ammonia in an alcohol, preferably ethanol. The product is isolated and purified by conventional means.

Step 3—Preparation of Compounds of Formula (24)

To prepare compounds of Formula (24), the amidine of Formula (23) is reacted with about 1 to 1.5 molar equivalents, preferably about 1.3 molar equivalents, of acetylacetaldehyde dimethylacetal in a protic solvent (for example methanol, ethanol, propanol, preferably methanol), and about 1 to 1.5 molar equivalents, preferably about 1.1 molar equivalents, of sodium methoxide, at a temperature of about 40°–90° C., preferably at about 65° C., for about 4–32 hours, preferably about 16 hours. When the reaction is substantially complete, the compound of Formula (24) is isolated and purified by conventional means, preferably flash chromatography.

Step 4—Preparation of Compounds of Formula (25)

To prepare compounds of Formula (25), the pyrimidine of Formula (24) is reacted with about 1 to 1.2 molar equivalents, preferably about 1.05 molar equivalents, of bromine. The reaction is conducted in a monocarboxylic acid, preferably acetic acid, at a temperature of about 50°–110° C., preferably at about 85° C., for about 20 minutes to 2 hours, preferably about 1 hour. When the reaction is substantially complete, the compound of Formula (25) is isolated and purified by conventional means, preferably recrystallization.

Step 5—Preparation of Compounds of Formula (IDB) where T and V are Nitrogen and U is CH To prepare compounds of Formula (IDB) where T and V are nitrogen and U is CH, the pyrimidine of Formula (25) is reacted with about 1 to 1.2 molar equivalents, preferably about 1 molar equivalents, of an amine of formula $HNR^2R^3$, in the presence of about 1–10 molar equivalents, preferably about 3 molar equivalents, of an inorganic base or tertiary organic base as defined above, preferably triethylamine. The reaction is conducted in an ethereal solvent as defined above, preferably tetrahydrofuran, at a temperature of about 20°–100° C., preferably at about 50° C., for about 4–32 hours, preferably about 16 hours. When the reaction is substantially complete, the compound of Formula (IDB) is isolated and purified by conventional means, preferably flash chromatography, followed by conversion to an acid salt, preferably a hydrochloride salt.

2. Alternatively, the compounds of Formula (IDB) where T and V are nitrogen and U is CH may be prepared from the amidine of Formula (23) as shown below in Reaction Scheme IX.

REACTION SCHEME IX

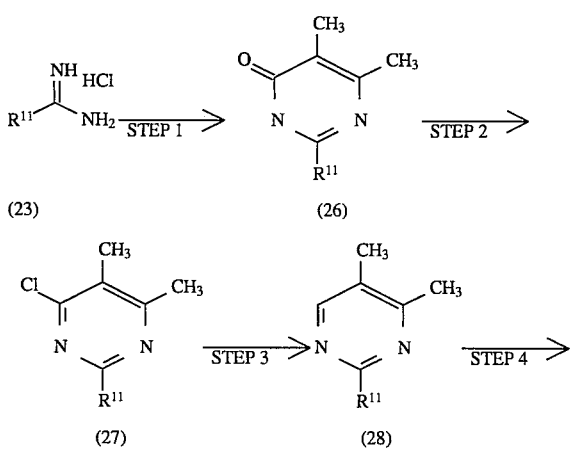

-continued
REACTION SCHEME IX

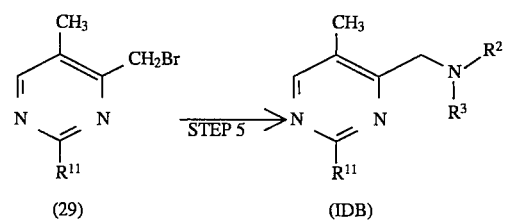

where $R^2$, $R^3$, and $R^{11}$ are as defined in the Summary of the Invention.

Step 1—Preparation of Compounds of Formula (26)

To prepare compounds of Formula (26), the amidine of Formula (23) is reacted with about 1 to 1.5 molar equivalents, preferably about 1.3 molar equivalents, of ethyl acetoacetate substituted in the alpha position by lower alkyl. The reaction is conducted in a protic solvent (for example methanol, ethanol, propanol, preferably ethanol), at a temperature of about 40°–100° C., preferably at about 80° C., for about 4–32 hours, preferably about 16 hours. When the reaction is substantially complete, the compound of Formula (26) is isolated and purified by conventional means, preferably crystallization.

Step 2—Preparation of Compounds of Formula

To prepare compounds of Formula (27), the pyrimidinone of Formula (26) is reacted with an excess of a halogenating agent (for example, thionyl chloride, phosphorus trichloride, phosphorus pentachloride, phosphorus oxychloride, preferably phosphorus oxychloride), at a temperature of about 60°–120° C., preferably at about 100° C., for about 10 minutes to 6 hours, preferably about 1 hour. When the reaction is substantially complete, the compound of Formula (27) is isolated and purified by conventional means, preferably crystallization.

Step 3—Preparation of Compounds of Formula (28)

To prepare compounds of Formula (28), the pyrimidine of Formula (27) is hydrogenated under about 1–5 atmospheres of hydrogen, preferably about 1 atmosphere, in the presence of a noble metal catalyst (for example platinum on carbon, platinum oxide, palladium on carbon, preferably palladium on carbon), in the presence of about 1–10 molar equivalents, preferably about 1.2 molar equivalents, of an organic base or inorganic base as defined above, preferably triethylamine, at a temperature of about 0°–40° C., preferably at about 25° C., for about 2–32 hours, preferably about 16 hours. When the reaction is substantially complete, the compound of Formula (28) is isolated and purified by conventional means.

Step 4—Preparation of Compounds of Formula (29)

The compounds of Formula (28) are converted to compounds of Formula (29) in the same manner as shown for the conversion of (24) to (25), in Reaction Scheme VIII, Step 4.

Step 5—Preparation of Compounds of Formula (IDB) where T and V are Nitrogen and U is CH The compounds of Formula (29) are converted to compounds of Formula (IDB) in the same manner as shown for the conversion of (25) to (IDB), in Reaction Scheme VIII, Step 5.

3. Alternatively, the compounds of Formula (IDB) where T and U are CH and V is nitrogen may be prepared as shown below in Reaction Scheme X.

REACTION SCHEME X

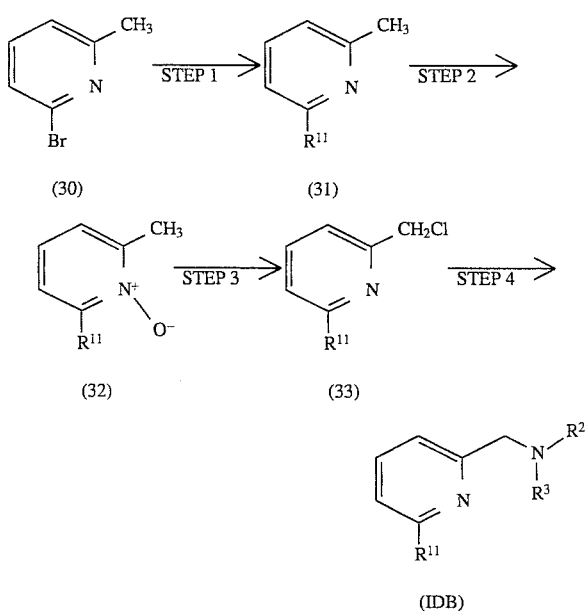

(IDB)

wherein $R^2$, $R^3$, and $R^{11}$ are as defined in the Summary of the Invention.

Starting Material

Compounds of Formula (30) can be made according to the method described in *J.A.C.S.*, Vol. 75, p5842 (1956).

Step 1—Preparation of Compounds of Formula (31)

The compounds of Formula (30) are converted to compounds of Formula (31) in the same manner as shown for the preparation of compounds of Formula (17), in Reaction Scheme V, Step 1.

Step 2—Preparation of Compounds of Formula (32)

To prepare compounds of Formula (32), the pyridine of Formula (31) is reacted with about 1 to 1.5 molar equivalents, preferably about 1 molar equivalents, of an oxidizing agent (for example, hydrogen peroxide, m-chloroperbenzoic acid, preferably m-chloroperbenzoic acid). The reaction is conducted in an inert solvent, preferably chloroform, at a temperature of about 0°–70° C., preferably at about 50° C., for about 1–12 hours, preferably about 2 hours. When the reaction is substantially complete, the N-oxide of Formula (32) is isolated and purified by conventional means, preferably flash chromatography.

Step 3—Preparation of Compounds of Formula (33)

To prepare compounds of Formula (33), the N-oxide of Formula (32) is reacted with about 1 to 1.5 molar equivalents, preferably about 1.1 molar equivalents, of a halogenating agent (for example, tosyl chloride, phosphorus oxychloride, thionyl chloride, preferably thionyl chloride), in the presence of about 1–1.5 molar equivalents, preferably about 1.1 molar equivalents, of an inorganic base or tertiary organic base as defined above, preferably triethylamine. The reaction is conducted in an inert solvent, preferably methylene chloride, at a temperature of about 20°–60° C., preferably at about 40° C., for about 5 minutes to 6 hours, preferably about 30 minutes. When the reaction is substantially complete, the compound of Formula (33) is isolated and purified by conventional means, preferably flash chromatography.

Step 4—Preparation of Compounds of Formula (IDB) where T and U are CH and V is Nitrogen The compounds of Formula (33) are converted to compounds of Formula (IDB) in the same manner as shown for the conversion of (25) to (IDB), in Reaction Scheme VIII, Step 5.

4. Alternatively, the compounds of Formula (IDB) where T and U are CH and V is nitrogen may be prepared as shown below in Reaction Scheme XI.

REACTION SCHEME XI

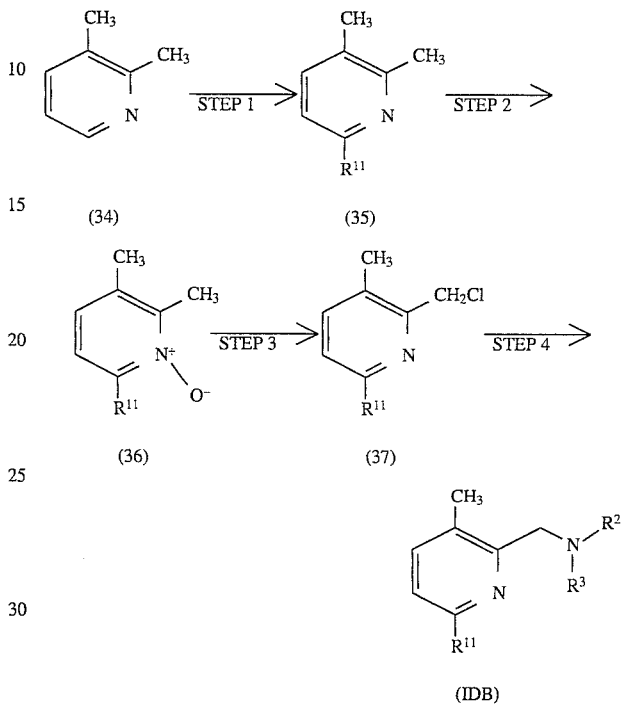

(IDB)

wherein $R^2$, $R^3$, and $R^{11}$ are as defined in the Summary of the Invention.

Step 1—Preparation of Compounds of Formula (35)

To prepare compounds of Formula (35), the pyridine of Formula (34) is reacted with about 1 to 1.5 molar equivalents, preferably about 1.2 molar equivalents, of a Grignard reagent of formula $R^{11}MgBr$, in the presence of about 1 to 1.5 molar equivalents, preferably about 1.1 molar equivalents, of a halochloroformate, preferably phenyl chloroformate. The reaction is conducted in an inert solvent, preferably tetrahydrofuran, at a temperature of about −60° C. for about 1 hour, followed by room temperature for about 6–24 hours, preferably about 16 hours. When the reaction is substantially complete, the resultant carbamate is separated conventionally, and treated about 1 to 1.5 molar equivalents, preferably about 1.1 molar equivalents, of an oxidizing agent (for example, dichlorodicyanobenzoquinone, chloranil, preferably o-chloranil), in an inert solvent, preferably toluene, and an organic acid, preferably acetic acid. The reaction is conducted at a temperature of about 0°–40° C., preferably about 25° C., for about 1 hour. When the reaction is substantially complete, the compound of Formula (35) is isolated and purified by conventional means, preferably flash chromatography.

Step 2—Preparation of Compounds of Formula (36)

The compounds of Formula (35) are converted to compounds of Formula (36) in the same manner as shown for the conversion of (31) to (32), in Reaction Scheme X, Step 2.

Step 3—Preparation of Compounds of Formula (37)

The compounds of Formula (36) are converted to compounds of Formula (37) in the same manner as shown for the conversion of (32) to (33), in Reaction Scheme X, Step 3.

Step 4—Preparation of Compounds of Formula (IDB)

The compounds of Formula (37) are converted to compounds of Formula (IDB) in the same manner as shown for the conversion of (33) to (IDB), in Reaction Scheme X, Step 4.

5. Alternatively, the compounds of Formula (IDB) where T and U are CH and V is N may be prepared as shown below in Reaction Scheme XII.

REACTION SCHEME XII

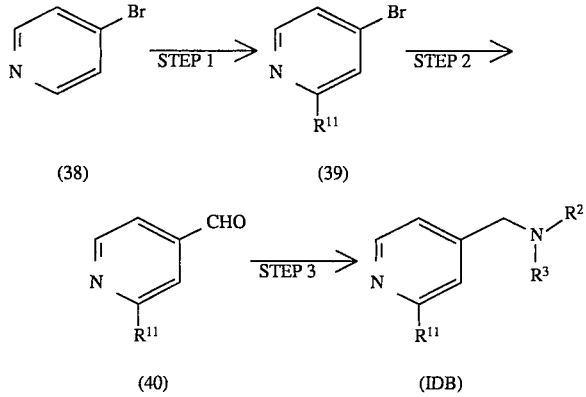

where $R^2$, $R^3$, and $R^{11}$ are as defined in the Summary of the Invention.

Step 1—Preparation of Compounds of Formula (39)

To prepare compounds of Formula (39), the pyridine of Formula (38) is reacted in the same manner as shown for the conversion of (34) to (35), in Reaction Scheme XI, Step 1. Alternatively, such compounds may be prepared as described in *J. Org. Chem.*, Vol. 50, p 4410 (1985).

Step 2—Preparation of Compounds of Formula (40)

To prepare compounds of Formula (40), the bromopyridine of Formula (39) is reacted with about 1 to 1.2 molar equivalents, preferably about 1.05 molar equivalents, of an alkyl lithium, preferably n-butyl lithium. The reaction is conducted in an inert solvent, preferably tetrahydrofuran, at a temperature of about −100° to −50° C., preferably about for about 15 minutes, followed by an excess of dimethylformamide at the same temperature, for about 1–10 hours, preferably about 2 hours. When the reaction is substantially complete, the compound of Formula (40) is isolated and purified by conventional means, preferably flash chromatography.

Step 3—Preparation of Compounds of Formula (IDB)

The compounds of Formula (40) are converted to compounds of Formula (IDB) in the same manner as shown for the conversion of (8) to (IA), in Reaction Scheme II, Step 6.

6. Alternatively, the N-oxide derivative of compounds of Formula (IDB) where T and U are CH and V is N may be prepared as shown below in Reaction Scheme XIII.

REACTION SCHEME XIII

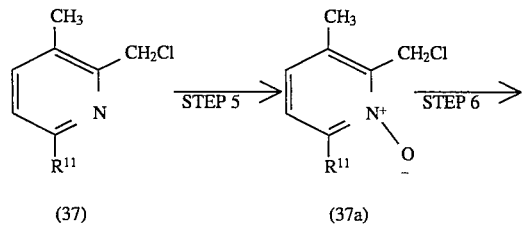

-continued
REACTION SCHEME XIII

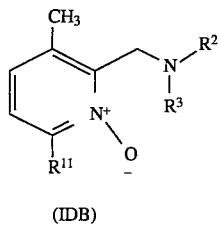

where $R^2$, $R^3$, and $R^{11}$ are as defined in the Summary of the Invention.

Step 5—Preparation of Compounds of Formula (37a)

The compounds of Formula (37) are converted to compounds of Formula (37a) in the same manner as shown for the conversion of (31) to (32), in Reaction Scheme X, Step 2.

Step 6—Preparation of Compounds of Formula (IDB)

The compounds of Formula (37a) are converted to compounds of Formula (IDB) in the same manner as shown for the conversion of (33) to (IDB), in Reaction Scheme X, Step 4.

Isolation and Purification of the Compounds

Isolation and purification of the compounds and intermediates described herein can be effected, if desired, by any suitable separation or purification procedure such as, for example, filtration, extraction, crystallization, column chromatography, thin-layer chromatography, thick-layer chromatography, preparative low or high-pressure liquid chromatography or a combination of these procedures. Specific illustrations of suitable separation and isolation procedures can be had by reference to the Examples hereinbelow. However, other equivalent separation or isolation procedures could, of course, also be used.

Salts of Compounds of Formula (I)

The compounds of Formula (I) may be converted to a corresponding acid addition salt by virtue of the presence of basic nitrogen atoms. The conversion is accomplished by treatment with at least a stoichiometric amount of an appropriate acid, such as hydrochloric acid, hydrobromic acid, sulfuric acid, nitric acid, phosphoric acid and the like, and organic acids such as acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, menthanesulfonic acid, ethanesulfonic acid, p-toluenesulfonic acid, salicylic acid and the like. Typically, the free base is dissolved in an inert organic solvent such as diethyl ether, ethyl acetate, chloroform, ethanol or methanol and the like, and the acid added in a similar solvent. The temperature is maintained at 0°–50° C. The resulting salt precipitates spontaneously or may be brought out of solution with a less polar solvent.

In summary, the compounds of the present invention are made by the procedures outlined below:

1. A process for preparing compounds of Formula (IA), wherein:

m is 0;

$R^1$ is hydrogen;

$R^2$ is hydrogen, or lower alkyl;

$R^3$ is

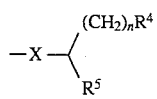

or $R^2$ and $R^3$ taken together with the nitrogen atom to which they are attached represent a group of the formula:

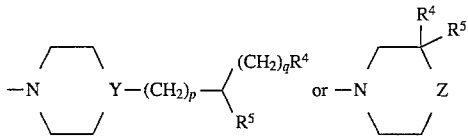

wherein:

n is 0 or 1;

p is 0, 1, 2 or 3;

q is 0 or 1;

$R^4$ is hydrogen, or optionally substituted phenyl;

$R^5$ is optionally substituted phenyl;

X is $(CH_2)_p$, or 4-piperidin-1-yl;

Y is CH, CH—O—, CH—S—, or nitrogen;

Z is $CH_2$, NH, sulfur, or oxygen; and

A is:

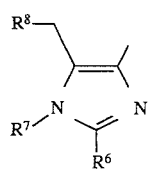

wherein:

$R^6$ is lower alkyl, or optionally substituted phenyl;

$R^7$ is hydrogen or lower alkyl;

$R^8$ is hydrogen, lower alkyl, or optionally substituted phenyl;

constitutes:

reacting a compound of the formula:

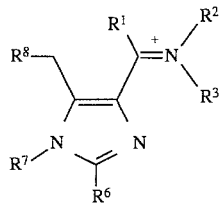

where $R^1$ is hydrogen and $R^2$, $R^3$, $R^6$, $R^7$, and $R^8$ are as defined above;

with a reducing agent.

2. A process for preparing compounds of Formula (IA), wherein:

$R^7$ is $R^{14}C(O)OCH(R^{13})$—, and;

m, $R^1$, $R^2$, $R^3$, $R^6$, and $R^8$ are as defined in the Summary of the Invention;

constitutes reacting a compound of the formula:

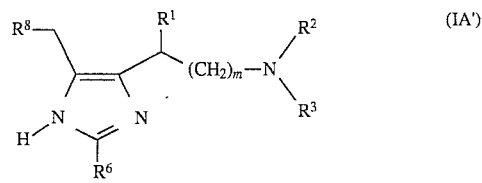

with a compound of the formula $R^{14}C(O)OCH(R^{13})L$, where L is chloro, bromo, or iodo, and $R^{13}$ and $R^{14}$ are as defined in the Summary of the Invention, in the presence of a base.

3. A process for preparing compounds of Formula (IB), wherein:

m is 0;

$R^1$ is hydrogen;

$R^2$, $R^3$ are as defined above; and

A is:

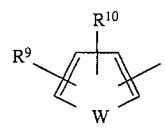

wherein:

$R^9$ is lower alkyl, or optionally substituted phenyl;

$R^{10}$ is hydrogen, or lower alkyl; and

W is oxygen, sulfur, or $NR^{15}$;

wherein $R^{15}$ is hydrogen or lower alkyl; constitutes reacting a compound of the formula:

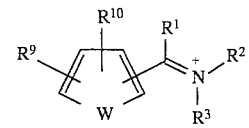

where $R^1$ is hydrogen and $R^2$, $R^3$, $R^9$, and $R^{10}$ are as defined above;

with a reducing agent.

4. A process for preparing compounds of Formula (IB), wherein:

m is 0;

$R^1$ is lower alkyl; and

A, $R^2$, $R^3$ are as defined in Part 3 above;

constitutes reacting a compound of the formula:

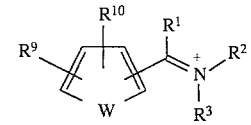

where $R^1$ is hydrogen and $R^2$, $R^3$, $R^9$, and $R^{10}$ are as defined above;

with a Grignard reagent of the formula $R^1MgBr$.

5. A process for preparing compounds of Formula (IB), wherein:

m is 1;

$R^1$ is hydroxy; and

A, $R^2$, $R^3$ are as defined in Part 3 above;

constitutes reacting a compound of the formula:

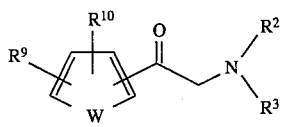 (11)

where $R^2$, $R^3$, $R^9$, and $R^{10}$ are as defined above;
with a reducing agent.

6. A process for preparing compounds of Formula (IC), wherein:

m is 0;
$R^1$ is hydrogen;
$R^2$, $R^3$ are as defined above; and
A is:

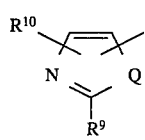

where Q is oxygen or sulfur; and
$R^9$ and $R^{10}$ are as defined above;
constitutes reacting a compound of the formula:

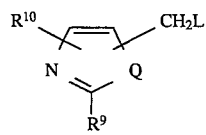 (14)

where Q, $R^9$ and $R^{10}$ are as defined above;
with an amine of the formula $HNR^2R^3$, where $R^2$ and $R^3$ are as defined above, in the presence of a base.

7. A process for preparing compounds of Formula (IDA), wherein:

m is 0;
$R^1$ is hydrogen;
$R^2$, $R^3$ are as defined above; and
A is:

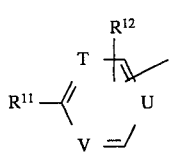

where:
$R^{11}$ is lower alkyl or optionally substituted aryl;
$R^{12}$ is hydrogen, lower alkyl, lower alkoxy, halo, or trifluoromethyl;
T, U, and V are CH;
constitutes reacting a compound of the formula:

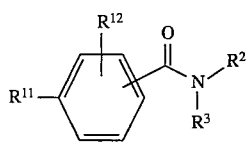 (19)

where $R^2$, $R^3$, $R^{11}$, and $R^{12}$ are as defined above;
with a reducing agent, for example lithium aluminum hydride.

8. A process for preparing compounds of Formula (ID), wherein:
m is 0;

$R^1$ is hydrogen;
$R^2$, $R^3$ are as defined above; and
A is:

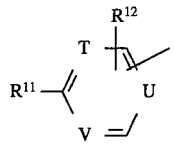

where:
$R^{11}$ is lower alkyl or optionally substituted aryl;
$R^{12}$ is hydrogen, lower alkyl, lower alkoxy, halo, or trifluoromethyl; and
T, U, and V are independently CH, or nitrogen;
constitutes reacting a compound of the formula:

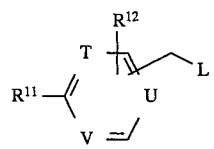

where L is a leaving group, for example chloro, bromo, iodo, methanesulfonate, or p-toluenesulfonate;
with an amine of the formula $HNR^2R^3$, where $R^2$ and $R^3$ are as defined above, in the presence of a base.

9. Alternatively, a process for preparing compounds of Formula I where A, m, $R^1$, $R^2$, and $R^3$ are as defined in the Summary of the Invention, constitutes:

(a) reacting the free base of a compound of Formula I with an acid to give a pharmaceutically acceptable acid addition salt; or (b) reacting an acid addition salt of a compound of Formula I with a base to give the corresponding free base; or (c) converting an acid addition salt of a compound of Formula I to another pharmaceutically acceptable acid addition salt of Formula I.

10. Alternatively, a process for preparing an N-oxide of compounds of Formula I where A, m, $R^1$, $R^2$, and $R^3$ are as defined in the Summary of the Invention, constitutes reacting a compound of Formula (I) with an oxidizing agent.

Utility and Methods of Administration

General Utility

The compounds of this invention are useful for treating mammals having a variety of vascular disease states, and have protective activity against some of the deleterious effects resultant upon cerebral ischemia. The compounds are useful for treating mammals having a disease treated by direct neuronal protection or a disease treated by calcium channel inhibition, sodium channel inhibition, or inhibition of both calcium and sodium channels, including:

diseases treated by direct neuronal protection, such as ischaemia including focal and global ischaemia, cerebral ischaemia including ischaemia-induced neurodegeneration, perinatal asphyxia, spinal injuries, peripheral nerve ischaemia, peripheral nerve damage, head trauma, primary intracerebral hemorrhage, encephalopathy, epilepsy or epileptic psychotic symptoms, and neurological diseases such as Alzheimer's, Huntington's chorea, Parkinsons and dementias; and diseases treated by calcium channel inhibition, sodium channel inhibition, or inhibition of both calcium and sodium channels, including:

diseases treated by inhibiting cerebrovascular vasospasm and by cerebrovascular vasodilation, such as migraine, stroke, vasospasm due to subarachnoid hemorrhage, and cerebrovascular ischaemia induced by cocaine abuse;

diseases treated by inhibiting cellular oedema, such as cerebral oedema and hyponatraemic encephalopathy;

cardiovascular diseases, such as hypertension, angina, stable and unstable angina, Prinzmetal angina, arrhythmia, thrombosis, myocardial infarction, embolism, and congestive heart failure such as chronic or acute cardiac failure;

diseases characterized by ischaemia of lower legs due to peripheral vascular disease, including intermittent claudication;

diseases characterized by spasms of smooth muscle, including reversible airways obstruction, asthma, spasms of the ureter, spasms of the bladder, uterine cramps, and irritable bowel syndrome;

prevention of vasoconstriction and/or ischemic tissue damage during a surgical procedure, such as bypass grafts, angiography, angioplasty, organ preservation during transplant, hypertensive crisis, or post-operative hypertension;

diseases treated by diuresis; and uraemic encephalopathy,

Generally, vascular disease states are found in mammals, including: domestic commercial animals such as horses, cattle, sheep and pigs; domestic house animals such as dogs, cats, and the like; and particularly humans.

Activity Testing

Affinity for sodium channels and interaction with sodium and calcium currents can be determined in vitro, and activity for treating cerebrovascular disease states can be determined in vivo by ascertaining the neuroprotective effect. Sodium channel affinity is determined in vitro by measuring the displacement of [$^3$H]-batrachotoxin from its binding sites on the sodium channel, as shown in Example 18.

Sodium and calcium channel activities are determined in vitro by whole cell voltage-clamp recordings of sodium and channel currents, as shown in Example 19.

In vivo activity can be determined according to the mouse model of focal ischaemia (the mouse middle cerebral artery occlusion, or "MCA" model) Gotti, B. et al., Brain Res, 1990, 522, 290–307. The MCA model entails an indirect measure of neuronal cell death following an ischemic event (i.e., occlusion of the left middle cerebral artery), as described in Example 20 below.

General Administration

The compounds of this invention are administered at a therapeutically effective dosage, i.e., a dosage sufficient to provide treatment for the disease states previously described. Administration of the active compounds and salts described herein can be via any of the accepted modes of administration for agents that serve similar utilities.

Generally, a daily dose of from 0.02 to 50 mg/kg of body weight per day of the active compound of Formula I. Most conditions respond to treatment comprising a dosage level on the order of 0.1 to 4 mg/kilogram of body weight per day. Thus, for administration to a 70 kg person, the dosage range would be about 1.4 to 3500 mg per day, preferably about 7.0 to 280 mg per day.

Depending on the specific disease state, administration can be via any accepted systemic route, for example, via parenteral, oral, intravenous, or nasal routes, in the form of solid, semi-solid or liquid dosage forms, such as for example, tablets, suppositories, pills, capsules, powders, solutions, suspensions, aerosols, emulsions or the like, preferably in unit dosage forms suitable for simple administration of precise dosages. The compositions will include a conventional pharmaceutical carrier or excipient and an active compound of Formula (I) and, in addition, may include other medicinal agents, pharmaceutical agents, carriers, adjuvants, etc.

If desired, the pharmaceutical composition to be administered may also contain minor amounts of non-toxic auxiliary substances such as wetting or emulsifying agents, pH buffering agents and the like, such as for example, sodium acetate, sorbitan monolaurate, triethanolamine oleate, etc.

The compounds of this invention are generally administered as a pharmaceutical composition which comprises a pharmaceutical excipient in combination with a compound of Formula (I). The level of the drug in a formulation can vary within the full range employed by those skilled in the art, e.g., from about 0.01 percent weight (% w) to about 99.99% w of the drug based on the total formulation and about 0.01% w to 99.99% w excipient. Preferably, the formulation will be about 3.5 to 60% by weight of the pharmaceutically active compound, with the rest being suitable pharmaceutical excipients.

Oral Administration

The preferred manner of administration, for the conditions detailed above, is oral using a convenient daily dosage regimen which can be adjusted according to the degree of affliction. For such oral administration, a pharmaceutically acceptable, non-toxic composition is formed by the incorporation of any of the normally employed excipients, such as, for example, pharmaceutical grades of mannitol, lactose, starch, magnesium stearate, sodium saccharine, talcum, cellulose, glucose, gelatin, sucrose, magnesium carbonate, and the like. Such compositions take the form of solutions, suspensions, tablets, pills, capsules, powders, sustained release formulations and the like. Such compositions may contain between 0.01 wt/% and 99.99 wt/% of the compound of Formula (I), but preferably such compositions will contain between 25 wt/% and about 80 wt/%.

Preferably the compositions will take the form of a pill or tablet and thus the composition will contain, along with the active ingredient, a diluent such as lactose, sucrose, dicalcium phosphate, and the like; a disintegrant such as starch or derivatives thereof; a lubricant such as magnesium stearate and the like; and a binder such as a starch, polyvinylpyrrolidone, gum acacia, gelatin, cellulose and derivatives thereof, and the like.

Suppositories

For systemic administration via suppository, traditional binders and carriers include, for example, polyalkaline glycol or triglycerides [e.g., PEG 1000 (96%) and PEG 4000 (4%)]. Such suppositories may be formed from mixtures containing active ingredients in the range of from about 0.5 wt/% to about 10 wt/%; preferably from about 1 wt/% to about 2 wt/%.

Liquids

Liquid pharmaceutically administrable compositions can, for example, be prepared by dissolving, dispersing, etc. an active compound (about 0.5% to about 20%), as described above, and optional pharmaceutical adjuvants in a carrier, such as, for example, water, saline, aqueous dextrose, glycerol, ethanol and the like, to thereby form a solution or suspension.

Actual methods of preparing such dosage forms are known, or will be apparent, to those skilled in this art; for example, see *Remington's Pharmaceutical Sciences*, Mack Publishing Company, Easton, Pa., 16th Ed., 1980. The composition to be administered will, in any event, contain a quantity of the active compound(s) in a pharmaceutically effective amount for relief of the particular condition being treated in accordance with the teachings of this invention.

EXAMPLES

The following preparations and examples are given to enable those skilled in the art to more clearly understand and practice the present invention. They should not be considered as a limitation on the scope of the invention, but merely as being illustrative and representative of the preferred embodiments of the present invention.

Unless specified to the contrary, these preparations and examples are carried out under an inert atmosphere, for example nitrogen or argon.

PREPARATION 1

Preparation of Compounds of Formula (6)

A. Preparation of (6) where $R^6$ is 4-Trifluoromethylphenyl, $R^7$ is Methyl, and $R^8$ is Hydrogen A mixture of methyl trifluoromethanesulfonate (3.3 ml) and p-trifluoromethylbenzonitrile (5.17 g) was heated at 65° C. for 3½ hours, then cooled to 5° C. The mixture was then dissolved in 10 ml of acetonitrile, and 2 ml of propargylamine in 10 ml of acetonitrile was added. The mixture was stirred at room temperature for 16 hours, then cooled to 5° C. and 3 ml of concentrated sodium hydroxide added (about 1 equivalent), followed by 40 ml of methylene chloride. The organic layer was separated, the solvent evaporated under reduced pressure, and 50 ml of toluene added. The mixture was refluxed for 3 hours, cooled, the solvent evaporated under reduced pressure, and the residue recrystallized from isopropyl ether, to yield 4.6g of 1,5-dimethyl-2-(4-trifluoromethylphenyl)imidazole, a compound of Formula (6), m.p. 130° C.

B. Preparation of (6), varying $R^6$, $R^7$ and $R^8$

Similarly, following the procedures of Preparation 1A above, but optionally replacing methyl trifluoromethanesulfonate with other compounds of formula $R^7Cl$ in the presence of $FeCl_3$, or $R^7SO_3CF_3$, and optionally replacing p-trifluoromethylbenzonitrile with other compounds of Formula (1), and optionally replacing propargylamine with other compounds of Formula (4), the following intermediates of Formula (6) were prepared:
1-ethyl-5-methyl-2-(4-trifluoromethylphenyl)-imidazole, m.p. 93° C.;
1-isopropyl-5-methyl-2-(4-trifluoromethylphenyl)imidazole, m.p. 86° C.;
1-(sec-butyl)-5-methyl-2-(4-trifluoromethylphenyl)imidazole, m.p. 100° C.;
1,5-dimethyl-2-phenylimidazole, m.p. 55° C.;
1,2,5-trimethylimidazole, oil;
1,5-dimethyl-2-n-butylimidazole, m.p. 76° C.;
1,5-dimethyl-2-(4-methoxyphenyl)imidazole, m.p. 99°–100° C.
1,5-dimethyl-2-(4-chlorophenyl)imidazole, m.p. 108° C.; and
1,5-dimethyl-2-(tert-butyl)imidazole, m.p. 40° C.

PREPARATION 2

Preparation of Compounds of Formula (7)

A. Preparation of (7) where $R^6$ is 4-Trifluoromethylphenyl, $R^7$ is Methyl, and $R^8$ is Hydrogen A mixture of 1,5-dimethyl-2-(4-trifluoromethylphenyl)imidazole (0.6 g), aqueous formaldehyde (3.5 ml of 36%), sodium acetate (0.6 g), and acetic acid (0.5 ml) was refluxed for 24 hours. The mixture was cooled, and concentrated sodium hydroxide added until the mixture was just basic, keeping the temperature at about 10° C. The mixture was extracted with methylene chloride, and solvent removed from the organic layer under reduced pressure. The residue was flash-chromatographed on silica gel, eluting with methylene chloride containing methanol (97/3), to yield 0.4 g of 1,5-dimethyl-4-hydroxymethyl- 2-(4-trifluoromethyl-phenyl)imidazole, m.p. 152° C.

B. Preparation of (7), varying $R^6$, $R^7$ and $R^8$

Similarly, following the procedures of Preparation 2A above, but replacing 1,5-dimethyl-2-(4-trifluoromethylphenyl)imidazole with other compounds of Formula (6), the following intermediates of Formula (7) are prepared:
1-ethyl-4-hydroxymethyl-5-methyl-2-(4-trifluoromethylphenyl)-imidazole, m.p. 158° C.;
1-isopropyl-4-hydroxymethyl-5-methyl-2-(4-trifluoromethylphenyl)-imidazole, m.p. 160° C.;
1-(sec-butyl)-4-hydroxymethyl-5-methyl-2-(4-trifluoromethylphenyl)-imidazole, m.p. 150° C.;
1,5-dimethyl-4-hydroxymethyl-2-phenylimidazole;
4-hydroxymethyl-1,2,5-trimethylimidazole;
1,5-dimethyl-4-hydroxymethyl-2-n-butylimidazole; and
1,5-dimethyl-4-hydroxymethyl-2-(4-methoxyphenyl)imidazole.

PREPARATION 3

Preparation of Compounds of Formula (8)

A. Preparation of (8) where $R^6$ is 4-Trifluoromethylphenyl, $R^7$ is Methyl, and $R^8$ is Hydrogen A mixture of 1,5-dimethyl-4-hydroxymethyl-2-(4-trifluoromethylphenyl)imidazole (0.5 g) and manganese dioxide (2 g) in 20 ml of chloroform was refluxed for 24 hours. A further 2 g of manganese dioxide was added, and the mixture refluxed for a further 3 hours. The mixture was cooled, the solid material filtered off, and washed with methylene chloride. The solvent was removed from the filtrate under reduced pressure, to yield 0.5 g of 1,5-dimethyl-4-formyl-2-(4-trifluoromethylphenyl)imidazole, m.p. 144° C.

B. Preparation of (8), varying $R^6$, $R^7$ and $R^8$

Similarly, following the procedures of Preparation 3A above, but replacing 1,5-dimethyl-4-hydroxymethyl-2-(4-trifluoromethyl-phenyl)imidazole with other compounds of Formula (7), the following intermediates of Formula (8) are prepared:
1-ethyl-4-formyl-5-methyl-2-(4-trifluoromethylphenyl)imidazole, oil;
1-isopropyl-4-formyl-5-methyl-2-(4-trifluoromethylphenyl)imidazole, m.p. 145° C.;
1-(sec-butyl)-4-formyl-5-methyl-2-(4-trifluoromethylphenyl)imidazole, oil;
1,5-dimethyl-4-formyl-2-phenylimidazole;
4-formyl-1,2,5-trimethylimidazole;
1,5-dimethyl-4-formyl-2-n-butylimidazole; and
1,5-dimethyl-4-formyl-2-(4-methoxyphenyl)imidazole.

PREPARATION 4

Preparation of Compounds of Formula (9a)

A. Preparation of (9a) where $R^9$ is 5-(4-Methylphenyl), $R^{10}$ is 3-Methyl, W is Oxygen, and —CHO is in the 2-Position Phosphorus oxychloride (12 ml) was added slowly to dimethylformamide (9.85 ml) with stirring at 0° C., and the mixture stirred at 0° C. for 30 minutes. A solution of 3-methyl-5-(4-methylphenyl)furan (22 g) in 50 ml of dichloroethane was added dropwise over a period of 15 minutes, maintaining the temperature at 0° C. The mixture was then stirred at room temperature for 1½ hours. Ice water was then added, and the pH of the aqueous layer adjusted to about 8 with dilute sodium hydroxide. The organic layer was separated, the aqueous layer extracted with dichloromethane, the organic portions combined and solvent removed under reduced pressure. The solvent was removed from the filtrate under reduced pressure, and the residue flash chromatographed on silica gel, eluting with 10% ethyl acetate in heptane, to yield 19.2 g of 2-formyl-3-methyl-5-(4-methylphenyl)furan.

B. Preparation of (9a) varying $R^9$, $R^{10}$, W, and the Position of the Formyl Group Similarly, following the procedures of Preparation 4A above, but replacing 3-methyl-5-(4-methylphenyl)furan with other compounds of Formula (9), the following intermediates of Formula (9a) were prepared:
2-formyl-3-methyl-5-(n-butyl)furan, as an oil;
2-formyl-3-methyl-5-(t-butyl)furan, as an oil;
2-formyl-3-methyl-5-phenylfuran, m.p. 55° C.;
2-formyl-3-methyl-5-(4-trifluoromethylphenyl)furan, m.p. 80° C.;
2-formyl-3-methyl-5-cyclohexylfuran, as an oil;
2-formyl-3-methyl-5-phenylpyrrole, m.p. 152°–3° C.;
3-formyl-2-methyl-5-phenylpyrrole, m.p. 150° C.;
3-formyl-1,2-dimethyl-5-phenylpyrrole, m.p. 97° C.;
2-formyl-1,3-dimethyl-5-phenylpyrrole, m.p. oil;
2-formyl-3-methyl-5-phenylthiophene, m.p. 110° C.; and
3-formyl-2-methyl-5-phenylthiophene, m.p. 82°–3° C.

PREPARATION 5

Preparation of Compounds of Formula (17)

A. Preparation of (17) where $R^{11}$ is 4-Methylphenyl, $R^{12}$ is Hydrogen, and R is Ethyl Magnesium (1.6 g) and p-bromotoluene (10.26 g) in 60 ml of tetrahydrofuran were stirred and warmed until the reaction commenced. When the exothermic reaction had finished, the mixture was refluxed overnight. In a separate flask, 4 ml of DIBAL (1M in toluene) was added to a suspension of bis(triphenylphosphine)palladium(II) chloride (1.4 g) in 100 ml of tetrahydrofuran, followed by ethyl 3-iodobenzoate (11.04 g). To this mixture, the magnesium reagent prepared above was added dropwise, causing an exothermic reaction. The reaction mixture was stirred overnight at room temperature, and then quenched by addition of dilute hydrochloric acid. The mixture was extracted with ether, and the organic layer washed with water, and then saturated brine. The organic layer was separated, dried over sodium sulfate, the solvent evaporated under reduced pressure, and the residue chromatographed on silica gel, eluting with 5% ethyl acetate in heptane, to yield 5.69 g of ethyl 4'-methylbiphenyl-3-carboxylate, a compound of Formula (17), as a pale yellow oil.

B. Preparation of (17) where R is Ethyl, varying $R^{11}$ and $R^{12}$

Similarly, following the procedures of Preparation 5A above, but optionally replacing p-bromotoluene with other arylhalo precursors to Formula (15), and optionally replacing ethyl 3-iodobenzoate with other compounds of Formula (16), the following intermediates of Formula (17) were prepared:
ethyl 4,4'-dimethylbiphenyl-3-carboxylate;
ethyl 4-methyl-4'-fluorobiphenyl-3-carboxylate;
ethyl 4-methyl-4'-trifluoromethylbiphenyl-3-carboxylate;
ethyl 4-methyl-4'-methoxybiphenyl-3-carboxylate;
ethyl 4'-methoxybiphenyl-3-carboxylate;
ethyl 4'-dimethylaminobiphenyl-3-carboxylate; and
ethyl 4-methyl-3'-methoxybiphenyl-3-carboxylate.

PREPARATION 6

Preparation of Compounds of Formula (18)

A. Preparation of (18) where $R^{11}$ is 4-Methylphenyl, and $R^{12}$ is Hydrogen To a solution of ethyl 4'-methylbiphenyl-3-carboxylate (4.0 g) in ethanol (50 ml) was added a solution of 10 ml of 10% aqueous sodium hydroxide, and the mixture refluxed for 2 hours. Solvent was removed under reduced pressure, water added to the residue, and the solution filtered. The filtrate was acidified with dilute hydrochloric acid, and the white solid filtered off and dried under vacuum, yielding 2.4 g of 4'-methylbiphenyl-3-carboxylic acid m.p. 192° C.

B. Preparation of (18), varying $R^{11}$ and $R^{12}$

Similarly, following the procedures of Preparation 6A above, but replacing ethyl 3-(4-methylphenyl)benzoate with other compounds of Formula (17), the following intermediates of Formula (18) are prepared:
4,4'-dimethylbiphenyl-3-carboxylic acid;
4-methyl-4'-fluorobiphenyl-3-carboxylic acid;
4-methyl-4'-trifluoromethylbiphenyl-3-carboxylic acid;
4-methyl-4'-methoxybiphenyl-3-carboxylic acid;
4'-methoxybiphenyl-3-carboxylic acid;
4'-dimethylaminobiphenyl-3-carboxylic acid; and
4-methyl-3'-methoxybiphenyl-3-carboxylic acid.

PREPARATION 7

Preparation of Compounds of Formula (19)

A. Preparation of (19) where —$NR^2R^3$ represents Diphenylmethylpiperazine, $R^{11}$ is 4-Methylphenyl, and $R^{12}$ is Hydrogen To a suspension of 4'-methylbiphenyl-3-carboxylic acid (2.2 g) in a mixture of methylene chloride (20 ml) and dimethylformamide (0.5 ml) was added thionyl chloride (1.48 g). The mixture was refluxed until the suspension dissolved, after which the temperature was allowed to cool to room temperature. To this solution was added 1-(diphenylmethyl)piperazine (3.94 g) in methylene chloride dropwise, and the reaction mixture allowed to stand overnight. Sodium hydroxide (30 ml of 1N) and 50 ml of methylene chloride was added, the organic layer separated, washed with brine, dried over sodium sulfate, and solvent removed under reduced pressure. The residue was chromatographed on silica gel, eluting with 25% ethyl acetate in heptane, to yield 3.8 g of 1-diphenylmethyl-4-(4'-methylbiphenyl-3-carbonyl)piperazine. The dihydrochloride salt was prepared and recrystallized from ethanol, m.p. 226° C.

B. Preparation of (19), varying —$NR^2R^3$, $R^{11}$ and $R^{12}$

Similarly, following the procedures of Preparation 7A above, but replacing 4'-methylbiphenyl-3-carboxylic acid with other compounds of Formula (18), the following intermediates of Formula (19) are prepared:
1-diphenylmethyl-4-(4,4'-dimethylbiphenyl-3-carbonyl)piperazine;
1-diphenylmethyl-4-(4-methyl-4'-fluorobiphenyl-3-carbonyl)piperazine;

1-diphenylmethyl-4-(4-methyl-4'-trifluoromethylbiphenyl-3-carbonyl)piperazine;
1-diphenylmethyl-4-(4-methyl-4'-methoxybiphenyl-3-carbonyl)piperazine;
1-diphenylmethyl-4-(4'-methoxybiphenyl-3-carbonyl)piperazine;
1-diphenylmethyl-4-(4'-dimethylaminobiphenyl-3-carbonyl)piperazine; and
1-diphenylmethyl-4-(4-methyl-3'-methoxybiphenyl-3-carbonyl)piperazine.

PREPARATION 8

Preparation of Compounds of Formula (13) and (20)

A. Preparation of (20) where $R^{11}$ is 4-Methylphenyl, and $R^{12}$ is 4-Methyl To a suspension of lithium aluminum hydride (0.2 g) in 50 ml of ether at 0° C. was added dropwise a solution of ethyl 4,4'-dimethylbiphenyl-3-carboxylate (2 g) in ether. After the addition was complete, the mixture was allowed to slowly rise to room temperature, and stirred for 2 hours. Excess reagent was hydrolysed with wet sodium sulfate. The mixture was filtered, the solvent evaporated from the filtrate under reduced pressure, and the residue flash-chromatographed on silica gel, eluting with 25% ethyl acetate in heptane, to yield 3-hydroxymethyl-4,4'-dimethylbiphenyl as an oil.

B. Preparation of (20), varying $R^{11}$ and $R^{12}$

Similarly, following the procedures of Preparation 8A above, but replacing ethyl 4,4'-dimethylbiphenyl-3-carboxylate with other compounds of Formula (17), the following intermediates of Formula (20) were prepared:
3-hydroxymethyl-4-methyl-4'-fluorobiphenyl, as an oil;
3-hydroxymethyl-4-methyl-4'-trifluoromethylbiphenyl, m.p. 92° C.;
3-hydroxymethyl-4'-methoxybiphenyl, m.p. 91° C.;
3-hydroxymethyl-4-methylbiphenyl, as an oil;
3-hydroxymethyl-4'-methylbiphenyl, as an oil;
3-hydroxymethyl-4'-dimethylaminobiphenyl, m.p. 94° C.;
3-hydroxymethyl-4-methyl-3'-methoxybiphenyl, as an oil;
3-hydroxymethyl-4-methyl-4'-methoxybiphenyl, m.p. 85° C.;
4-hydroxymethyl-4'-methylbiphenyl, m.p. 130° C.; and
4-hydroxymethyl-4,4'-dimethylbiphenyl, oil.

C. Preparation of (13) where $R^9$ is 4-Methylphenyl, and $R^{10}$ is 5-Methyl

Similarly, following the procedures of Preparation 8A above, but replacing ethyl 4,4'-dimethylbiphenyl-3-carboxylate with compounds of Formula (12), the following intermediates of Formula (13) were prepared:
4-hydroxymethyl-2-(4-methylphenyl)-5-methyl-1,3-oxazole;
5-hydroxymethyl-2-(4-methylphenyl)-4-methyl-1,3-oxazole;
4-hydroxymethyl-2-(4-methylphenyl)-5-methyl-1,3-thiazole, m.p. 137° C.; and
5-hydroxymethyl-2-(4-methylphenyl)-4-methyl-1,3-thiazole, m.p. 100° C.

PREPARATION 9

Preparation of Compounds of Formula (14)

A. Preparation of (14) where $R^9$ is 4-Methylphenyl, $R^{10}$ is 5-Methyl, O is oxygen, and L is chloro A solution of 4-hydroxymethyl-2-(4-methylphenyl)-5-methyl-1,3-oxazole (3 g) in 30 ml of dichloromethane was cooled to 0° C., and thionyl chloride (1.75 g) added dropwise. The reaction was stirred for 1 hour at room temperature, then washed twice with dilute sodium bicarbonate solution, the organic layer separated, dried over sodium sulfate, and the solvent evaporated under reduced pressure, to yield 4-chloromethyl-2-(4-methylphenyl)-5-methyl-1,3-oxazole, which was used in the next reaction without further purification.

B. Preparation of (14) where $R^9$ is 4-Methylphenyl, and $R^{10}$ is 4-Methyl

Similarly, following the procedures of Preparation 9A above, but replacing 4-hydroxymethyl-2-(4-methylphenyl)-5-methyl-1,3-oxazole with other compounds of Formula (13), the following intermediate of Formula (14) was prepared:
5-chloromethyl-2-(4-methylphenyl)-4-methyl-1,3-oxazole;
4-chloromethyl-2-(4-methylphenyl)-5-methyl-1,3-thiazole; and
5-chloromethyl-2-(4-methylphenyl)-4-methyl-1,3-thiazole.

PREPARATION 10

Preparation of Compounds of Formula (24)

A. Preparation of (24) where $R^{11}$ is 4-Trifluoromethylphenyl (i) Preparation of (22)

A solution of p-trifluoromethylbenzonitrile (25 g) in 100 ml of ethanol was prepared, cooled to 0° C., and hydrochloric acid gas passed into the solution for 4 hours. The mixture was stirred for 10 hours at room temperature, then 200 ml of isopropyl ether added. The mixture was cooled to 0° C. for 30 minutes, then the solvent removed under reduced pressure. The resulting crystals were washed with isopropyl ether, giving 33.4 g of 4-trifluoromethylbenziminoethyl ether hydrochloride, m.p. 144° C.

ii) Preparation of (23)

Ethanol (300 ml) was saturated with ammonia, and cooled below 10° C. 4-Trifluoromethylbenziminoethyl ether (33.4 g) was added in portions to the stirred solution, and the mixture allowed to stand at room temperature for 24 hours. The solvent was evaporated off under reduced pressure, 200 ml of isopropyl acetate added, the mixture cooled to 0° C., and the solid filtered off and washed several times with isopropyl acetate, giving 27.3 g of 4-trifluoromethylbenzamidine hydrochloride, m.p. 184° C.

iii) Preparation of (24)

To a solution of 4-trifluoromethylbenzamidine (45 g) was added sodium methoxide (11.9 g) as a solid in portions, followed by acetylaldehyde dimethylacetal (34.3 g). The mixture was refluxed overnight, then filtered, the solvent evaporated from the filtrate under reduced pressure, and the residue was partitioned between methylene chloride and water, the organic layer separated, washed with brine, dried over sodium sulfate, the solvent evaporated under reduced pressure, and the residue flash-chromatographed on silica gel, eluting with 20% ethyl acetate in heptane, to yield 13 g of 4-methyl-2-(4-trifluoromethylphenyl)pyrimidine m.p. 50° C.

B. Preparation of (24) where $R^{11}$ is 4-Methylphenyl

Similarly, following the procedures of Preparation 10A(i), (ii) and (iii) above, but replacing p-trifluoromethylbenzonitrile with p-methylbenzonitrile, the following intermediate of Formula (24) is prepared:

4-methyl-2-(4-methylphenyl)pyrimidine.

PREPARATION 11

Preparation of Compounds of Formula (26)

A. Preparation of (26) where $R^{11}$ is 4-Methylphenyl

To a solution of 4-methylbenzamidine (4.4 g) in 30 ml of ethanol was added ethyl 2-methylacetoacetate (6.1 g), and the mixture refluxed for 4 hours, giving a precipitate. The mixture was cooled to 0° C., the solid filtered off, washed with ethanol, and dried under reduced pressure, yielding 6 g of 5,6-dimethyl-2-(4-methylphenyl)-3H-pyrimidin-4-one, m.p. 250° C.

PREPARATION 12

Preparation of Compounds of Formula (27)

A. Preparation of (27) where $R^{11}$ is 4-Methylphenyl

A mixture of 5,6-dimethyl-2-(4-methylphenyl)-3H-pyrimidin-4-one (6 g) and phosphorus oxychloride (40 ml) was refluxed for 2 hours. Excess phosphorus oxychloride was removed under reduced pressure, ice added to the residue, and the mixture extracted with methylene chloride, the organic layer washed with brine, dried over sodium sulfate, the solvent evaporated under reduced pressure, to yield 6.2 g of 4,5-dimethyl-6-chloro-2-(4-methylphenyl)pyrimidine, m.p. 165° C.

PREPARATION 13

Preparation of Compounds of Formula (28)

A. Preparation of (28) where $R^{11}$ is 4-Methylphenyl

A mixture of 4,5-dimethyl-6-chloro-2-(4-methylphenyl)pyrimidine (6.2 g), triethylamine (3.2), and palladium on carbon (200 mg) in 100 ml of methanol was stirred overnight under hydrogen. Methylene chloride was added, the solid filtered off through celite, and solvent removed from the filtrate under reduced pressure. Tetrahydrofuran was added to the residue, and triethylamine hydrochloride filtered off. Solvent was removed from the filtrate under reduced pressure, giving 4.4 g of 4,5-dimethyl-2-(4-methylphenyl)pyrimidine, m.p. 114° C.

PREPARATION 14

Preparation of Compounds of Formula (25) and (29)

A. Preparation of (25) where $R^{11}$ is 4-Trifluoromethylphenyl

A mixture of 4-methyl-2-(4-trifluoromethylphenyl)pyrimidine (3 g) and bromine (2.11 g) in 20 ml of acetic acid was warmed to 80° C. for 1 hour, and then allowed to cool to room temperature. Ether (10 ml) was added, and the precipitate filtered off and washed with ether, giving 3.3 g of 4-bromomethyl-2-(4-trifluoromethylphenyl)pyrimidine, m.p. 125° C.

B. Preparation of (29) where $R^{11}$ is 4-Methylphenyl

Similarly, following the procedures of Preparation 14A above, but replacing 4-methyl-2-(4-trifluoromethylphenyl)pyrimidine with 4,5-dimethyl-2-(4-methylphenyl)pyrimidine, the following intermediate of Formula (29) was prepared:

4-bromomethyl-2-(4-methylphenyl)-5-methylpyrimidine, m.p. 176° C.

PREPARATION 15

Preparation of Compounds of Formula (31) and (39)

A. Preparation of (31) where $R^{11}$ is 4-Methylphenyl

Magnesium (1.6 g) and p-bromotoluene (10.2 g) in 100 ml of tetrahydrofuran were stirred and warmed until the reaction commenced. When the exothermic reaction had finished, the mixture was refluxed for 1 hour. In a separate flask, a solution of palladium(II)bis(triphenylphosphine)dichloride (1.4 g) in 60 ml of tetrahydrofuran was prepared, and 4 ml of DIBAL (1M in toluene) added, followed by 2-bromopicoline (6.9 g). To this mixture, the magnesium reagent prepared above was added dropwise, causing an exothermic reaction. The reaction mixture was stirred overnight at room temperature, and then quenched by addition of ether/water. The mixture was washed with dilute hydrochloric acid, water, and then saturated brine. The organic layer was separated, dried over sodium sulfate, the solvent evaporated under reduced pressure, and the residue chromatographed on silica gel, eluting with 30–50% methylene chloride in heptane, to yield 4.5 g of 2-(4-methylphenyl)-6-methylpyridine, a compound of Formula (31), as an oil.

B. Preparation of (39) where $R^{11}$ is 4-Methylphenyl

Similarly, following the procedures of Preparation 15A above, but replacing 2-bromopicoline by 4-bromopyridine hydrochloride, the following intermediate of Formula (39) was prepared:

4-bromo-2-(4-methylphenyl)pyridine, m.p. 64° C.

PREPARATION 16

Preparation of Compounds of Formula (32) and (36)

A. Preparation of (32) where $R^{11}$ is 4-Methylphenyl

A solution of 2-(4-methylphenyl)-6-methylpyridine (4.5 g) in 100 ml of chloroform was cooled to 0° C., and m-chloroperbenzoic acid (7.7 g) in 50 ml of chloroform was added over a period of 15 minutes. The mixture was stirred at room temperature for 3 hours, then at 50° C. for 2 hours, followed by stirring overnight at room temperature. Solvent was evaporated to a small volume under reduced pressure, and the residue passed through an alumina column, eluting with 2% methanol in methylene chloride to remove benzoic acid. The eluate was flash-chromatographed on silica gel, eluting with 5% methanol in methylene chloride, to yield 2.8 g of 2-(4-methylphenyl)-6-methylpyridine-N-oxide, m.p. 95° C.

B. Preparation of (36) where $R^{11}$ is 4-Methylphenyl

Similarly, following the procedures of Preparation 16A above, but replacing 2-(4-methylphenyl)-6-methylpyridine by 2,3-dimethyl-6-(4-methylphenyl)pyridine, the following intermediate of Formula (36) was prepared:

2,3-dimethyl-6-(4-methylphenyl)pyridine-N-oxide, m.p. 126° C.

PREPARATION 17

Preparation of Compounds of Formula (33) and (37)

A. Preparation of (33) where $R^{11}$ is 4-Methylphenyl

To a solution of 2-(4-methylphenyl)-6-methylpyridine-N-oxide (2.8 g) in 10 ml of chloroform was added simultaneously phosphorus oxychloride (1.48 ml) in 10 ml of chloroform and triethylamine (2.22 ml) in 10 ml of chloroform, over a period of 15 minutes. An exothermic reaction took place initially, and then the mixture was refluxed for a further 30 minutes. The mixture was then cooled, washed with ice-water, the solvent evaporated under reduced pressure, and the residue flash-chromatographed on silica gel, eluting with 33% methylene chloride in heptane, to yield 1 g of 2-(4-methylphenyl)-6-chloromethylpyridine, m.p. 94° C.

B. Preparation of (37) where $R^{11}$ is 4-Methylphenyl

Similarly, following the procedures of Preparation 17A above, but replacing 2-(4-methylphenyl)-6-methylpyridine-N-oxide by 2,3-dimethyl-6-(4-methylphenyl)pyridine-N-oxide, the following intermediate of Formula (37) was prepared:

2-chloromethyl-3-methyl-6-(4-methylphenyl)pyridine, as an oil.

PREPARATION 18

Preparation of Compounds of Formula (35)

A. Preparation of (35) where $R^{11}$ is 4-Methylphenyl

A solution of p-bromotoluene (13.5 g) in 50 ml of tetrahydrofuran was added to magnesium (1.5 g) and 1 crystal of iodine in a little tetrahydrofuran, and the mixture was refluxed for 1 hour. In a separate flask, a solution of 2,3-lutidine (6.5 g) in 100 ml of tetrahydrofuran was cooled to about −60° C., and the magnesium complex prepared above added, followed by phenyl chloroformate (8 ml). The mixture was stirred for 1 hour at −60° C., then at room temperature overnight. The solvent was removed under reduced pressure, the residue partitioned between ether and 200 ml of 20% ammonium chloride, the organic layer washed with water, followed by dilute hydrochloric acid. The solvent was evaporated under reduced pressure, and the residue flash-chromatographed on silica gel, eluting with 1% ethyl acetate in heptane, to yield 12.4 g of 1,6-dihydro-2,3-dimethyl-6-(4-methylphenyl)-1-phenoxycarbonyl pyridine, m.p. 106° C.

The benzoate was then dissolved in 150 ml of toluene, and a solution of o-chloranil (10.4 g) in 90 ml of acetic acid added. After 30 minutes, the solvents were evaporated under reduced pressure, and the residue partitioned between methylene chloride and water, and made basic with sodium hydroxide solution. The organic layer was washed several times with water, the solvent evaporated under reduced pressure, and the residue flash-chromatographed on silica gel, eluting with 1% ethyl acetate in heptane, to yield 2.8 g of 2,3-dimethyl-6-(4-methylphenyl)pyridine, m.p. 76° C.

PREPARATION 19

Preparation of Compounds of Formula (40)

A. Preparation of (40) where $R^{11}$ is 4-Methylphenyl

A solution of 4-bromo-2-(4-methylphenyl)pyridine (3.2 g) in 30 ml of tetrahydrofuran was cooled to −70° C., and 1.6M n-butyl lithium (8.1 ml) was added. The solution was stirred for 15 minutes at −70° C., and then dimethylformamide (1.3 ml) added. The mixture was allowed to warm slowly to room temperature over a period of 2 hours, and aqueous saturated ammonium chloride solution added. The mixture was partitioned between methylene chloride and water, the organic layer separated and dried over sodium sulfate, the solvent evaporated under reduced pressure, and the residue flash-chromatographed on silica gel, eluting with 20% ethyl acetate in heptane, to yield 0.81 g of 4-formyl-2-(4-methylphenyl)pyridine, m.p. 66° C.

EXAMPLE 1

Preparation of Compounds of Formula (IA) and (IB)

A. Preparation of (IA) where m is 0, $R^1$ is Hydrogen, —$NR^2R^3$ represents 1-(2,3,4-Trimethoxyphenyl)methylpiperazine, $R^6$ is 4-Trifluoromethylphenyl, $R^7$ is Methyl, and $R^8$ is Hydrogen A solution of 1,5-dimethyl-4-formyl-2-(4-trifluoromethylphenyl)imidazole (0.5 g), 1-(2,3,4-trimethoxyphenylmethyl)piperazine (0.54 g), and titanium(IV)isopropoxide (0.73 g) was allowed to stand for 1 hour at room temperature. Ethanol (10 ml) was added, and the resultant solution was stirred for 1 hour. Sodium cyanoborohydride (90 mg) was then added, and the mixture stirred overnight. Sodium hydroxide was then added until the pH was just over 7, the solvent removed under reduced pressure, and the residue partitioned between methylene chloride/water. The mixture was filtered, the organic layer separated, dried over anhydrous magnesium sulfate, filtered and evaporated. The residue was flash-chromatographed on silica gel, eluting with ethyl acetate/methanol/ammonia (97/3/0.5), to yield 0.45 g of 1-(2,3,4-trimethoxyphenyl)methyl-4-[(2-(4-trifluoromethylphenyl)- 1,5-dimethylimidazol-4-yl)methyl]piperazine. Treatment with anhydrous hydrochloric acid in ethanol converted the base to its dihydrochloride salt, m.p. 235° C.

B. Preparation of (IA), where m is 0 and $R^1$ is Hydrogen, varying —$NR^2R^3$, $R^6$, $R^7$ and $R^8$ Similarly, following the procedures of Example 1A above, but optionally replacing 1,5-dimethyl-4-formyl-2-(4-trifluoromethylphenyl)imidazole with other compounds of Formula (8), and optionally replacing 1-(2,3,4-trimethoxyphenylmethyl)piperazine with amines of formula $HNR^2R^3$, the following compounds of Formula (IA) were prepared:

1-diphenylmethyl-4-[(2-(4-trifluoromethylphenyl)-1,5-dimethylimidazol- 4-yl)methyl]piperazine dihydrochloride, m.p. 205° C.;

1-(2,3,4-trimethoxyphenyl)methyl-4-[(2-(4-trifluoromethylphenyl)- 1-ethyl-5-methylimidazol-4-yl)methyl]piperazine dihydrochloride, m.p. 215° C.;

1-diphenylmethyl-4-[(2-(4-trifluoromethylphenyl)-1-ethyl-5-methylimidazol- 4-yl)methyl]piperazine dihydrochloride, m.p. 200° C.;

1-(2,3,4-trimethoxyphenyl)methyl-4-[(2-(4-trifluoromethylphenyl)-1-isopropyl- 5-methylimidazol-4-yl)methyl] piperazine dihydrochloride, m.p. 210° C.;

1-diphenylmethyl-4-[(2-(4-trifluoromethylphenyl)-1-isopropyl-5-methylimidazol- 4-yl)methyl]piperazine dihydrochloride, m.p. 212° C.;

1-diphenylmethyl-4-[(2-(4-trifluoromethylphenyl)-1-(secbutyl)-5-methylimidazol- 4-yl)methyl]piperazine dihydrochloride, m.p. 212° C.;

2,2-di(4-fluorophenyl)-4-[(2-(4-methylphenyl)-4(5)-methyl- 1H-imidazol-(5)4-yl)methyl]morpholine dihydrochloride, m.p. 214° C.;

2,2-di(4-fluorophenyl)-4-[(2-(4-trifluoromethylphenyl)-4(5)-methyl- 1H-imidaz-(5)4-yl)methyl]morpholine dihydrochloride, m.p. 230° C.;

N-[2-(4-methylphenyl)-4(5)-methyl-1H-imidazol-5(4)-ylmethyl]-N-methyl- 3,3-diphenylpropylamine dihydrochloride, m.p. 200° C.;

N-[2-(4-methylphenyl)-4(5)-methyl-1H-imidazol-5(4)-ylmethyl]-N-methyl- 4,4-diphenylbutylamine dihydrochloride, m.p. 190° C.;

N-[2-(4-trifluoromethylphenyl)-4(5)-methyl-1H-imidazol-5(4)-ylmethyl]-N-methyl- 3,3-diphenylpropylamine dihydrochloride, m.p. 214° C.;

N-[2-(4-trifluoromethylphenyl)-4(5)-methyl-1H-imidazol-5(4)-ylmethyl]-N-methyl- 4,4-diphenylbutylamine dihydrochloride, m.p. 150° C.; and N-[2-(4-trifluoromethylphenyl)-4(5)-methyl-1H-imidazol-5(4)-ylmethyl]-N-methyl- 5,5-diphenylpentylamine dihydrochloride, m.p. 160° C.

C. Preparation of (IB), where m is 0 and $R^1$ is Hydrogen, varying —$NR^2R^3$, $R^9$ and $R^{10}$ Similarly, following the procedures of Example 1A above, but replacing 1,5-dimethyl-4-formyl-2-(4-trifluoromethylphenyl)imidazole with compounds of Formula (9a), and optionally replacing 1-(2,3,4-trimethoxyphenylmethyl)piperazine with amines of formula $HNR^2R^3$, the following compounds of Formula (IB) were prepared:

1-diphenylmethyl-4-[(5-phenyl-3-methylfuran-2-yl)methyl]piperazine dihydrochloride, m.p. 170° C.;

1-diphenylmethyl-4-[(5-n-butyl-3-methylfuran-2-yl)methyl]piperazine dihydrochloride, m.p. 145° C.;

1-diphenylmethyl-4-[(5-t-butyl-3-methylfuran-2-yl)methyl]piperazine dihydrochloride, m.p. 160° C.;

1-diphenylmethyl-4-[(5-cyclohexyl-3-methylfuran-2-yl)methyl]piperazine, m.p. 120° C.; m.p. dihydrochloride 184° C.;

1-diphenylmethyl-4-[(5-(4-trifluoromethylphenyl)-3-methylfuran-2-yl)methyl]piperazine, m.p. 150° C.; m.p. dihydrochloride 180° C.;

1-diphenylmethyl-4-[(5-(4-methylphenyl)-3-methylfuran-2-yl)methyl]piperazine dihydrochloride, m.p. 225° C.;

1-diphenylmethyl-4-[(5-(4-methoxyphenyl)-3-methylfuran-2-yl)methyl]piperazine fumarate, m.p. 216°–218° C.;

4-diphenylmethyl-1-[(5-phenyl-3-methylfuran-2-yl)methyl]piperidine dihydrochloride, m.p. 250° C.;

4-diphenylmethyl-1-[(5-(4-trifluoromethylphenyl)-3-methylfuran-2-yl)methyl]piperidine dihydrochloride, m.p. 240° C.;

1-(2,3,4-trimethoxyphenyl)methyl-4-[(5-(4-trifluoromethylphenyl)-3-methylfuran-2-yl)methyl]piperazine dihydrochloride, m.p. 230° C.;

4-(4-fluorophenyl)methyl-1-[(5-(4-methylphenyl)-3-methylfuran-2-yl)methyl]piperidine dihydrochloride, m.p. 210° C.;

2,2-di(4-fluorophenyl)-4-[(5-(4-methylphenyl)-3-methylfuran-2-yl)methyl]morpholine dihydrochloride, m.p. 210° C.;

1-diphenylmethyl-4-[(5-phenyl-3-methylpyrrol-2-yl)-methyl]piperazine, m.p. 60°–63° C.; maleate salt, m.p. 149°–152° C.;

1-diphenylmethyl-4-[(5-phenyl-2-methylpyrrol-3-yl)methyl]piperazine maleate, m.p. 180° C.;

1-diphenylmethyl-4-[(5-phenyl-1,2-dimethylpyrrol-3-yl)methyl]piperazine dihydrochloride, m.p. 225° C.;

1-(2,3,4-trimethoxyphenyl)methyl-4-[(5-phenyl-1,2-dimethylpyrrol-3-yl)methyl]piperazine dihydrochloride, m.p. 205° C.; 1-diphenylmethyl-4-[(5-phenyl-1,3-dimethylpyrrol-2-yl)methyl]piperazine, m.p. 151°–152° C.; maleate salt m.p. 159°–162° C.;

1-(2,3,4-trimethoxyphenyl)methyl-4-[(3-methyl-5-phenylthiophen-2-yl)methyl]piperazine dihydrochloride, m.p. 180° C.;

1-diphenylmethyl-4-[(3-methyl-5-phenylthiophen-2-yl)methyl]piperazine dihydrochloride, m.p. 179° C.;

4-diphenylmethyl-1-[(3-methyl-5-phenylthiophen-2-yl)methyl]piperidine dihydrochloride, m.p. 250° C.;

4-di(4-fluorophenyl)methyl-1-[(3-methyl-5-phenylthiophen-2-yl)oxymethyl]piperidine dihydrochloride, m.p. 135° C.;

1-diphenylmethyl-4-[(2-methyl-5-phenylthiophen-3-yl)methyl]piperazine dihydrochloride, m.p. 179°–181° C.; and 4-diphenylmethyl-1-[(2-methyl-5-phenylthiophen-3-yl)methyl]piperidine dihydrochloride, m.p. 155° C.

EXAMPLE 2

Preparation of compounds of Formula (IA)

A. Preparation of (IA) where m is 0, $R^1$ is Hydrogen, —$NR^2R^3$ represents 1-(Diphenylmethyl)piperazine, $R^6$ is 4-Trifluoromethylphenyl, $R^7$ is Hydrogen, and $R^8$ is Hydrogen To 300 ml of ethanol was added 13.7 g of 4(5)-methyl-2-(4-trifluoromethylphenyl)- 1H-imidazole, 15.3 g of N-(diphenylmethyl)piperazine, and 30 ml of 37% aqueous formaldehyde. The mixture was refluxed for 1 hour, then cooled to room temperature. A solid precipitated out, which was filtered off and dried, to give 23.7 g (80%) of 1-diphenylmethyl-4-[(2-(4-trifluoromethylphenyl)-4-methyl-1H-imidazol- 5-yl)methyl]piperazine, m.p. 244° C.

B. Preparation of (IA), where m is 0 and $R^1$ is Hydrogen, varying —$NR^2R^3$, $R^6$, $R^7$ and $R^8$ Similarly, following the procedures of Example 2A above, but optionally replacing 4(5)-methyl-2-(4-trifluoromethylphenyl)-1H-imidazole with other compounds of Formula (6), and replacing N-(diphenylmethyl)piperazine with 1-(2,3,4-trimethoxyphenylmethyl)piperazine, the following compounds of Formula (IA) were prepared:

(±)-1-[(2,3,4-trimethoxyphenyl)eth-1-yl]-4-[(2-(4-trifluoromethylphenyl)- 4(5)-methyl-1H-imidazol-(5)4-yl)methyl]piperazine, m.p. 90°–91° C.; m.p. trihydrochloride 184° C.;

(R)(+)-1-[(2,3,4-trimethoxyphenyl)eth-1-yl]-4-[(2-(4-trifluoromethylphenyl)- 4(5)-methyl-1H-imidazol-(5)4-yl)methyl]piperazine trihydrochloride, m.p. 195° C., $[\alpha_D]$ =+33° (C=1.0, methanol);

(S)(−)-1-[(2,3,4-trimethoxyphenyl)eth-1-yl]-4-[(2-(4-trifluoromethylphenyl)- 4(5)-methyl-1H-imidazol-(5)4-yl)methyl]piperazine trihydrochloride, m.p. 191° C., $[\alpha_D]$ =−30° (C=1.0, methanol);

(±)-1-[(2,3,4-trimethoxyphenyl)-2-cyclopentyleth-1-yl]-4-[(2-( 4-trifluoromethylphenyl)-4(5)-methyl-1H-imidazol-(5)4-yl)methyl]piperazine trihydrochloride, m.p. 200° C.;

(±)-1-[(2,3,4-trimethoxyphenyl)-1-cyclopentylmeth-1-yl]-4-[(2-( 4-trifluoromethylphenyl)-4(5)-methyl-1H-imidazol-(5)4-yl)methyl]piperazine trihydrochloride, m.p. 190° C.;

(±)-1-[(2,3,4-trimethoxyphenyl)-2-methylprop-1-yl]-4-[(2-( 4-trifluoromethylphenyl)-4(5)-methyl-1H-imidazol-(5)4-yl)methyl]piperazine trihydrochloride, m.p. 210° C.;

(R)(+)-1-[(2,3,4-trimethoxyphenyl)-2-methylprop-1-yl]-4-[(2-( 4-trifluoromethylphenyl)-4(5)-methyl-1H-imidazol-(5)4-yl)methyl]piperazine trihydrochloride;

(S)(−)-1-[(2,3,4-trimethoxyphenyl)-2-methylprop-1-yl]-4-[(2-( 4-trifluoromethylphenyl)-4(5)-methyl-1H-imidazol-(5)4-yl)methyl]piperazine trihydrochloride;

(±)-1-[(2,3,4-trimethoxyphenyl)-1-cyclopropylmeth-1-yl]-4-[(2-( 4-trifluoromethylphenyl)-4(5)-methyl-1H-imidazol-(5)4-yl)methyl]piperazine trihydrochloride, m.p. 190° C.;

(R)(+)-1-[(2,3,4-trimethoxyphenyl)-1-cyclopropylmeth-1-yl]-4-[(2-( 4-trifluoromethylphenyl)-4(5)-methyl-1H-imidazol-(5)4-yl)methyl]piperazine trihydrochloride; and (S)(−)-1-[(2,3,4-trimethoxyphenyl)-1-cyclopropylmeth-1-yl]-4-[(2-( 4-trifluoromethylphenyl)-4(5)-methyl-1H-imidazol-(5)4-yl)methyl]piperazine trihydrochloride.

EXAMPLE 3

Preparation of Compounds of Formula (IA)

A. Preparation of (IA) where m is 2, $R^1$ is Hydrogen, —$NR^2R^3$ represents 1-(2,3,4-Trimethoxyphenyl)methylpiperazine, $R^6$ is 4-Trifluoromethylphenyl, $R^7$ is Methyl, and $R^8$ is Hydrogen a) A solution of 1,5-dimethyl-4-formyl-2-(4-trifluoromethylphenyl)imidazole (1.0 g), malonic acid (0.8 g) in 10 ml of pyridine and 1.5 ml of piperidine was refluxed for 2 hours, and then allowed to stand for 12 hours at room temperature without stirring. The mixture was poured onto ice water, and hydrochloric acid added until a pH of 5 was attained. The mixture was extracted with dichloromethane, the organic layer evaporated under reduced pressure, and the residue crystallized from diisopropyl ether, to give 1,5-dimethyl-4-(3-acrylic acid)- 2-(4-trifluoro-methylphenyl)imidazole m.p. 242° C.

b) A solution of 1,5-dimethyl-4-(3-acrylic acid)-2-(4-trifluoromethylphenyl)imidazole (4 g) in ethanol (40 ml) was stirred under hydrogen with palladium on carbon (0.6 g) at room temperature for 48 hours. The catalyst was filtered off, and solvent removed from the filtrate under reduced pressure, giving 1,5-dimethyl-4-(3-propionic acid)-2-(4-trifluoromethylphenyl)imidazole, m.p. 192° C.

c) A solution of 1,5-dimethyl-4-(3-propionic acid)-2-(4-trifluoromethylphenyl)imidazole (2 g) and dicyclohexylcarbodiimide (2.0 g) in dichloromethane (80 ml ) was stirred at room temperature, and 1-(2,3,4 -trimethoxyphenylmethyl)piperazine (2.5 g) was added. The mixture was refluxed for 16 hours, solvent removed from the mixture, and the residue flash chromatographed on silica gel, eluting with 2% methanol in dichloromethane, to give 2 g of 1-(2,3,4-trimethoxyphenyl)methyl-4-[(2-(4-trifluoromethylphenyl)- 1,5-dimethylimidazol-4-yl)-3-oxoprop-1-yl]piperazine.

d) A solution of lithium aluminum hydride (0.6 g) and 1-(2,3,4-trimethoxyphenyl)methyl-4-[(2-(4-trifluoromethylphenyl)- 1,5-dimethylimidazol-4-yl)-3-oxoprop-1-yl]piperazine (2 g) in 50 ml of tetrahydrofuran was refluxed for 48 hours Excess reagent was hydrolysed by cooling the mixture to 0° C. and adding wet tetrahydrofuran dropwise. The mixture was filtered, the solid washed with a mixture of 1:1 ethanol/isopropanol, solvent evaporated from the filtrate, and the residue flash-chromatographed on silica gel, eluting with 2% methanol in dichloromethane, to yield 400 mg of 1-(2,3,4-trimethoxyphenyl)methyl- 4-[(2-(4-trifluoromethylphenyl)-1,5-dimethylimidazol- 4-yl)prop-1-yl]piperazine, which was converted to its hydrochloride salt, m.p. 212° C.

B. Preparation of (IA) where m is 2, $R^1$ is Hydrogen, varying $R^6$, $R^7$, and $R^8$ Similarly, following the procedures of Example 3A above, but optionally replacing 1,5-dimethyl-4-formyl-2-(4-trifluoromethylphenyl)imidazole with other compounds of Formula (8), and optionally replacing 1-(2,3,4-trimethoxyphenylmethyl)piperazine with other amines of formula $HNR^2R^3$, any compound of Formula (IA) where m is 2 and $R^1$ is hydrogen may be prepared.

EXAMPLE 4

Preparation of Compounds of Formula (IA)

A. Preparation of (IA) where m is 0, $R^1$ is Hydrogen, —$NR^2R^3$ represents Diphenylmethylpiperazine, $R^6$ is 4-Methylphenyl, $R^7$ is Acetic Acid Methyl Ester, and $R^8$ is Hydrogen To a suspension of sodium hydride (2 g) in 100 ml of tetrahydrofuran at 0° C. was added dropwise a solution of 1-diphenylmethyl-4-[(2-(4-methylphenyl)-(4)5-methyl-1H-imidazol- 4-yl)methyl]piperazine (20 g) in 100 ml of tetrahydrofuran (and sufficient dimethylformamide to produce a solution). The mixture was stirred at room temperature for 1 hour, then acetic acid chloromethyl ester (7.8 g) added, and the mixture stirred at room temperature overnight. Ice water and dichloromethane was added, and the organic layer separated, and solvent removed under reduced pressure. The residue was flash-chromatographed on silica gel, eluting with methylene chloride/methanol/ammonia (250/50/10), to give 1-diphenylmethyl-4-[(2-(4-methylphenyl)-5-methyl-1-(acetic acid methyl ester)imidazol-4-yl)methyl]piperazine, a portion of which was converted to the methanesulfonate salt in isopropanol and diethyl ether, m.p. 140° C.

B. Preparation of (IA) where m is 0, $R^1$ is Hydrogen, —$NR^2R^3$ represents Diphenylmethylpiperazine, $R^6$ is 4-Methylphenyl, and $R^8$ is Hydrogen, varying $R^7$ Similarly, following the procedures of Example 4A above, but replacing acetic acid chloromethyl ester with other esters of formula $ClCH(R^{13})OC(O)R^{14}$, where $R^{13}$ and $R^{14}$ are as defined in the Summary of the Invention, the following compounds of Formula (IA) and (IB) were prepared:

1-diphenylmethyl-4-[(2-(4-methylphenyl)-5-methyl-1-(acetic acid n-propyl ester)imidazol-4-yl)methyl]piperazine methanesulfonate, m.p. 131° C.;

1-diphenylmethyl-4-[(2-(4-methylphenyl)-5-methyl-1-(acetic acid i-propyl ester)imidazol-4-yl)methyl]piperazine, m.p. 204° C.;

1-diphenylmethyl-4-[(2-(4-methylphenyl)-5-methyl-1-(ethoxycarbonyloxymethyl)imidazol- 4-yl)methyl]piperazine methanesulfonate, m.p. 120° C.; and 1-diphenylmethyl-4-[(2-(4-methylphenyl)-5-methyl-1-(acetic acid t-butyl ester)imidazol-4-yl)methyl]piperazine methanesulfonate, m.p. 168° C.

EXAMPLE 5

Preparation of Compounds of Formula (IB)

A. Preparation of (IB) where m is 0, $R^1$ is Methyl, —$NR^2R^3$ represents 1-(Diphenylmethyl)piperazine, $R^9$ is 2-Phenyl, and $R^{10}$ is 4-Methyl A solution of 2-phenyl-4-methyl-5-formylfuran (1.1 g), diphenylmethylpiperazine (1.5 g), and titanium(IV)isopropoxide (1.76 g) was stirred for 1¼ hours. Diethyl ether (20 ml) was added, and the resultant solution was stirred for 30 minutes. Methyl magnesium iodide (6 ml of 3M in ether) was then added dropwise, and the mixture stirred at room temperature for 1 hour. Ammonium chloride (20 ml of a saturated solution in water) was then added, followed by 300 ml of methylene chloride, and the mixture made basic with a solution of sodium bicarbonate. The residue was partitioned between methylene chloride/water, the organic layer separated, dried over anhydrous magnesium sulfate, filtered and evaporated. The residue was flash-chromatographed on silica gel, eluting with 15% ethyl acetate in heptane with a trace of ammonia, to yield 0.51 g of 1-(diphenylmethyl)-4-[(2-phenyl-4-methylfuran-5-yl)eth-1-yl]piperazine. Treatment with anhydrous hydrochloric acid in ethanol converted the base to its dihydrochloride salt, m.p. 205°–8° C.

EXAMPLE 6

Preparation of Compounds of Formula (IB)

A. Preparation of (IB) where m is 1, $R^1$ is Hydroxy, —$NR^2R^3$ represents 1-(Diphenylmethyl)piperazine, $R^9$ is 3-Phenyl, and $R^{10}$ is 2-Methyl 1. Preparation of (11) where $R^9$ is 3-Phenyl, and $R^{10}$ is 2-Methyl A solution of 5-acetyl-2-methyl-3-phenylfuran (3.8 g) in 50 ml of tetrahydrofuran was protected from UV light while pyrrolidone hydrotribromide (9.4 g) was added in small portions with stirring. The mixture was stirred overnight, maintaining protection from the UV light, at room temperature, the crystals filtered off, washed with tetrahydrofuran, and the filtrate evaporated under reduced pressure.

The product was combined with diphenylmethylpiperazine (4.8 g) and potassium carbonate (3 g) in isopropanol (50 ml), and the mixture refluxed for two hours. Solvent was removed under reduced pressure, 100 ml of dichloromethane added to the residue, and the precipitate filtered off. The solid was washed with methylene chloride, the combined organic phases combined and the solvent removed under reduced pressure. The residue was flash chromatographed, eluting with 20% ethyl acetate in heptane, to give 3.8 g of 1-(diphenylmethyl)-4-[(2-methyl- 3-phenylfuran-5-yl)acet-2-yl]piperazine, a compound of Formula (11).

2. Preparation of (IB) Where $R^1$ is Hydroxy, $R^9$ is 3-Phenyl, $R^{10}$ is 2-Methyl, and —$NR^2R^3$ represents 1-(Diphenylmethyl)piperazine The compound of Formula (11) (prepared in part 1) was dissolved in 100 ml of ethanol at 5°–10° C., and 1.3 g of sodium borohydride added. The mixture was stirred for 30 minutes, a further 1.3 g of sodium borohydride added, stirred for a further 30 minutes at 5°–10° C., then stirred for an further 30 minutes at room temperature. Water (50 ml) was added, and the solvent removed under reduced pressure. The residue was partitioned between methylene chloride and water, the organic layer separated, dried over anhydrous magnesium sulfate, filtered and evaporated. The product, a pale yellow oil, was triturated with isopropylether, to give 2.9 g of a white solid, 1-(diphenylmethyl)-4-[(2-methyl-3-phenylfuran-5-yl)-1-hydroxyethan-2-yl]piperazine. Treatment with anhydrous hydrochloric acid in ethanol converted the base to its dihydrochloride salt, m.p. 190° C.

B. Preparation of (ID) where m is 1, $R^1$ is Hydroxy, varying $R^2$, $R^3$, $R^9$, and $R^{10}$ Similarly, following the procedures of Example 6A, parts 1 and 2 above, but optionally replacing 5-acetyl-2-methyl-3-phenylfuran with other compounds of Formula (10), and optionally replacing diphenylmethylpiperazine with other amines of formula $HNR^2R^3$, the following compounds of Formula (IB) where $R^1$ is hydroxy and m is 1 were prepared:

1-(diphenylmethyl)-4-[(2-phenyl-5-methylfuran-4-yl)-1-hydroxyethan- 2-yl]piperazine, m.p. 140° C.;
1-(diphenylmethyl)-4-[(2-methylfuran-5-yl)-1-hydroxyethan- 2-yl]piperazine dihydrochloride, m.p. 197° C.;
1-(diphenylmethyl)-4-[(2,5-dimethylfuran-4-yl)-1-hydroxyethan- 2-yl]piperazine dihydrochloride, m.p. 195° C.; and
1-(diphenylmethyl)-4-[(2-phenyl-4-methylfuran-5-yl)-1-hydroxyethan- 2-yl]piperazine dihydrochloride, m.p. 144°–154° C.

EXAMPLE 7

Preparation of Compounds of Formula (IC)

A. Preparation of (IC) where m is 0, O is Oxygen, $R^1$ is Hydrogen, —$NR^2R^3$ represents 1-(Diphenylmethyl)piperazine, $R^9$ is 4-Methylphenyl, and $R^{10}$ is 5-Methyl A mixture of 4-chloromethyl-2-(4-methylphenyl)-5-methyl-1,3-oxazole (3.2 g), diphenylmethylpiperazine (3.7 g) and potassium carbonate (2.2 g) in 100 ml of acetonitrile was refluxed for two hours. Solvent was removed under reduced pressure, and the residue partitioned between dichloromethane and water. The organic phase was separated, and the solvent removed under reduced pressure. The residue was flash chromatographed, eluting with ethyl acetate/heptane 2/1, to give 4.9 g of 1-(diphenylmethyl)-4-[2-(4-methylphenyl)-5 -methyl-1,3-oxazol-4-yl)methyl]piperazine, a compound of Formula (IC). Treatment with anhydrous hydrochloric acid in ethanol converted the base to its dihydrochloride salt, m.p. 180° C.

B. Preparation of (IC) where m is 0, $R^1$ is Hydrogen, varying O, $R^9$, and $R^{10}$ Similarly, following the procedures of Example 7A above, but optionally replacing 4-chloromethyl-2-(4-methylphenyl)-5-methyl-1,3-oxazole with other compounds of Formula (14), and optionally replacing diphenylmethylpiperazine with other amines of formula $HNR^2R^3$, the following compounds of Formula (IC) were prepared:

1-(diphenylmethyl)-4-[2-(4-methylphenyl)-4-methyl-1,3-oxazol- 5-yl)methyl]piperazine dihydrochloride, m.p. 230° C.;
1-(diphenylmethyl)-4-[2-(4-methylphenyl)-5-methyl-1,3-thiazol- 4-yl)methyl]piperazine, m.p. 135° C.; and
1-(diphenylmethyl)-4-[2-(4-methylphenyl)-4-methyl-1,3-thiazol- 5-yl)methyl]piperazine, m.p. 145° C.

EXAMPLE 8

Preparation of Compounds of Formula (ID)

A. Preparation of (IDA) where m is 0, $R^1$ is Hydrogen, —$NR^2R^3$ represents 1-(Diphenylmethyl)piperazine, $R^{11}$ is 4-Methylphenyl, and $R^{12}$ is Hydrogen To a suspension of lithium aluminum hydride (0.13 g) in 50 ml of ether at 0° C. was added dropwise a solution of 1-diphenylmethyl-4-(4'-methylbiphenyl-3-carbonyl)piperazine (1 g) in a mixture of ether and tetrahydrofuran. After the addition was complete, the mixture was allowed to slowly rise to room temperature, and stirred for 1½ hours. Excess reagent was hydrolysed with wet sodium sulfate. The mixture was filtered, the solvent evaporated, and the residue flash-chromatographed on silica gel, eluting with 25% ethyl acetate in heptane, to yield 1-diphenylmethyl-4-[4'-methylbiphenyl-3-methyl]piperazine, which was converted to its dihydrochloride salt by treatment with anhydrous hydrochloric acid in ethanol, m.p. 206° C.

B. Preparation of (IDA) where m is 0, $R^1$ is Hydrogen, varying —$NR^2R^3$, $R^{11}$, and $R^{12}$ Similarly, following the procedures of Example 8A above, but replacing 1-diphenylmethyl-4-(4'-methylbiphenyl-3-carbonyl)piperazine with other compounds of Formula (19), the following compounds of Formula (IDA) are prepared:

1-diphenylmethyl-4-(4,4'-dimethylbiphenyl-3-methyl)piperazine;
1-diphenylmethyl-4-(4-methyl-4'-fluorobiphenyl-3-methyl)piperazine;
1-diphenylmethyl-4-(4-methyl-4'-trifluoromethylbiphenyl-3-methyl)piperazine;
1-diphenylmethyl-4-(4-methyl-4'-methoxybiphenyl-3-methyl)piperazine;
1-diphenylmethyl-4-(4'-methoxybiphenyl-3-methyl)piperazine;

1-diphenylmethyl-4-(4,4'-dimethylaminobiphenyl-3-methyl)piperazine; and 1-diphenylmethyl-4-(4-methyl-3'-methoxybiphenyl-3-methyl)piperazine.

EXAMPLE 9

Preparation of Compounds of Formula (ID)

A. Preparation of (IDA) where m is 0, $R^1$ is Hydrogen, $-NR^2R^3$ is 1-(Diphenylmethyl)piperazinemethyl in the 3-position, $R^{11}$ is 4-Methylphenyl, and $R^{12}$ is 4-Methyl A solution of 3-hydroxymethyl-4,4'-dimethylbiphenyl (1.3 g) and triethylamine (0.8 g) in methylene chloride (50 ml) was cooled to 0° C., and methanesulfonyl chloride (0.84 g) in methylene chloride was added dropwise. The mixture was allowed to warm to room temperature, and was stirred overnight. Ice/water was then added, the organic layer separated, the aqueous layer washed with methylene chloride, the organic layer washed with brine, dried over sodium sulfate, and the solvent evaporated under reduced pressure, to yield 3-chloromethyl-4,4'-dimethylbiphenyl as an oil.

This product was dissolved in acetonitrile, and added to 1-(diphenylmethyl)piperazine (1.85 g) and potassium carbonate (1 g) in acetonitrile (60 ml). The mixture was refluxed overnight, the solid filtered off, washed with methylene chloride, solvent removed from the filtrate under reduced pressure, and the residue flash-chromatographed on silica gel, eluting with 30% ethyl acetate in heptane, to yield 1-diphenylmethyl-4-[4,4'-dimethylbiphenyl-3-ylmethyl]piperazine, as an off-white solid, which was converted to its dihydrochloride salt by treatment with anhydrous hydrochloric acid in ethanol, m.p. 177° C.

B. Preparation of (IDA) where m is 0, $R^1$ is Hydrogen, varying $-NR^2R^3$, $R^{11}$ and $R^{12}$ Similarly, following the procedures of Example 9A above, but optionally replacing 3-hydroxymethyl-4,4'-dimethylbiphenyl with other compounds of Formula (17), and optionally replacing 1-(diphenylmethyl)piperazine with 1-(2,3,4-trimethoxyphenylmethyl)piperazine, the following compounds of Formula (IDA) were prepared:

1-(2,3,4-trimethoxyphenylmethyl)-4-[4,4'-dimethylbiphenyl-3-ylmethyl]piperazine dihydrochloride, m.p. 193° C.;

1-(2,3,4-trimethoxyphenylmethyl)-4-[4-methyl-4'-fluorobiphenyl-3-ylmethyl]piperazine dihydrochloride, m.p. 198° C.;

1-diphenylmethyl-4-[4-methyl-4'-trifluoromethylbiphenyl-3-ylmethyl]piperazine dihydrochloride, m.p. 157;

1-(2,3,4-trimethoxyphenylmethyl)-4-[4-methyl-4'-trifluoromethylbiphenyl-3-ylmethyl]piperazine dihydrochloride, m.p. 185° C.;

1-(2,3,4-trimethoxyphenylmethyl)-4-[4-methyl-4'-methoxybiphenyl-3-ylmethyl]piperazine dihydrochloride, m.p. 230° C.;

1-(2,3,4-trimethoxyphenylmethyl)-4-[4'-methoxybiphenyl-3-ylmethyl]piperazine dihydrochloride, m.p. 204° C.;

1-(2,3,4-trimethoxyphenylmethyl)-4-[4-methylbiphenyl-3-ylmethyl]piperazine dihydrochloride, m.p. 204° C.;

1-(2,3,4-trimethoxyphenylmethyl)-4-[4'-dimethylaminobiphenyl-3-ylmethyl]piperazine dihydrochloride, m.p. 232° C.;

1-(2,3,4-trimethoxyphenylmethyl)-4-[4-methyl-3'-methoxybiphenyl-3-ylmethyl]piperazine dihydrochloride, m.p. 194° C.;

1-(3,4,5-trimethoxyphenylmethyl)-4-[4-methyl-3'-methoxybiphenyl-3-ylmethyl]piperazine dihydrochloride, m.p. 220° C.;

N-[4-methyl-4'-methoxybiphenyl-3-methyl]-N-methyl-4,4-diphenylbutylamine hydrochloride, m.p. 93° C.;

N-[4-methyl-4'-methoxybiphenyl-3-methyl]-N-methyl-3-(2,3,4-trimethoxyphenyl)propylamine fumarate, m.p. 185° C.;

1-(2,3,4-trimethoxyphenylmethyl)-4-[3,4'-dimethylbiphenyl-4-ylmethyl]piperazine dihydrochloride, m.p. 220° C.;

1-(2,3,4-trimethoxyphenylmethyl)-4-[4'-methylbiphenyl-4-ylmethyl]piperazine dihydrochloride, m.p. 235° C.;

1-(2,3,4-trimethoxyphenylmethyl)-4-[4'-methylbiphenyl-3-ylmethyl]piperazine dihydrochloride, m.p. 125° C.;

1-(2,3,4-trimethoxyphenylmethyl)-4-[3-(3-furanyl)phenylmethyl]piperazine dihydrochloride, m.p. 183° C.;

1-(2,3,4-trimethoxyphenylmethyl)-4-[3-(4-pyridinyl)phenylmethyl]piperazine trihydrochloride, m.p. 198° C.;

1-(2,3,4-trimethoxyphenylmethyl)-4-[5-methyl-4'-methoxybiphenyl-3-ylmethyl]piperazine dihydrochloride, m.p. 230° C.;

1-(2,3,4-trimethoxyphenylmethyl)-4-[4-chloro-4'-methoxybiphenyl-3-ylmethyl]piperazine hydrochloride, m.p. 190° C.;

1-(2,3,4-trimethoxyphenylmethyl)-4-[4'-chlorobiphenyl-3-ylmethyl]piperazine dihydrochloride, m.p. 201° C.;

2,2-di-(4-fluorophenyl)-4-[4'-methoxybiphenyl-3-ylmethyl]]morpholine methanesulfonate, m.p. 202° C.;

1-(4-fluorophenylmethyl)-4-[4'-methoxybiphenyl-3-ylmethyl]piperazine dimethanesulfonate m.p. 202° C.;

1-(2,3,4-trimethoxyphenylmethyl)-4-[(3-(n-butylphenyl)methyl]piperazine dihydrochloride, m.p. 177° C.; and 1-(2,3,4-trimethoxyphenylmethyl)-4-[(3-(3-thiophenyl)phenylmethyl]piperazine dihydrochloride, m.p. 210° C.

EXAMPLE 10

Preparation of Compounds of Formula (ID)

A. Preparation of (IDB) where m is 0, $R^1$ is Hydrogen, $-NR^2R^3$ is 1-(Diphenylmethyl)piperazinemethyl in the 4-position, $R^{11}$ is 4-Trifluoromethylphenyl, $R^{12}$ is Hydrogen, and V is Nitrogen A mixture of 4-bromomethyl-2-(4-trifluoromethylphenyl)pyrimidine (1.5 g), 1-(diphenylmethyl)piperazine (0.95 g), and triethylamine (1.14 g) in 30 ml of tetrahydrofuran was stirred at about 50° C. overnight. The mixture was cooled to 0° C., filtered, solvent removed from the filtrate under reduced pressure, and the residue flash-chromatographed on silica gel, eluting with 20% ethyl acetate in heptane, to yield 1-diphenylmethyl-4-[2-(4-trifluoromethylphenyl)-pyrimidin-4-yl)methyl]piperazine, m.p. 146° C., which was converted to its dihydrochloride salt by treatment with anhydrous hydrochloric acid in ethanol, m.p. 184° C.

B. Preparation of (IDB) where m is 0, $R^1$ is Hydrogen, $-NR^2R^3$ is 1-(Diphenylmethyl)piperazine in the 4-position, $R^{11}$ is 4-Methylphenyl, and $R^{12}$ is 5-Methyl Similarly, following the procedures of Example 10A above, but optionally replacing 4-bromomethyl-2-(4-trifluoromethylphenyl)pyrimidine with other compounds of Formulae (25) or (29), and optionally replacing 1-(diphenylmethyl)piperazine with 1-(2,3,4-trimethoxyphenylmethyl)piperazine, the following compounds of Formula (IDB) were prepared:

1-diphenylmethyl-4-[2-(4-methylphenyl)-5-methylpyrimidin-4-yl)methyl]piperazine dihydrochloride, m.p. 254° C.;

1-(2,3,4-trimethoxyphenylmethyl)-4-[2-(4-methylphenyl)-5-methylpyrimidin-4-yl)methyl]piperazine dihydrochloride, m.p. 210° C.;

1-(2,3,4-trimethoxyphenylmethyl)-4-[2-(4-trifluoromethylphenyl)pyrimidin-4-yl)methyl]piperazine dihydrochloride, m.p. 225° C.;

1-diphenylmethyl-4-[2-(4-trifluoromethylphenyl)-5-methylpyrimidin-4-yl)methyl]piperazine dihydrochloride, m.p. 230° C.; and 1-(2,3,4-trimethoxyphenylmethyl)-4-[2-(4-trifluoromethylphenyl)-5-methylpyrimidin- 4-yl)methyl]piperazine dihydrochloride, m.p. 214° C.;

EXAMPLE 11

Preparation of Compounds of Formula (ID)

A. Preparation of (IDB) where m is 0, $R^1$ is Hydrogen, $-NR^2R^3$ is 1-(Diphenylmethyl)piperazine, $R^{11}$ is 4-Methylphenyl, $R^{12}$ is Hydrogen, and V and U are CH A mixture of 2-(4-methylphenyl)-6-chloromethylpyridine (1 g), 1-(diphenylmethyl)piperazine (1.2 g), and triethylamine (0.72 ml) in 70 ml of tetrahydrofuran was refluxed for 24 hours. The solvent was removed from the mixture under reduced pressure, and the residue partitioned between methylene and water. The organic layer was separated, dried over sodium sulfate, the solvent removed under reduced pressure, and the residue flash-chromatographed on silica gel, eluting with 2% methanol in methylene chloride, to yield 1-diphenylmethyl-4-[6-(4-methylphenyl)pyridin-2-yl)methyl]piperazine, m.p. 140° C., which was converted to its dihydrochloride salt by treatment with anhydrous hydrochloric acid in ethanol, m.p. 240° C.

B. Preparation of (IDB) where m is 0, $R^1$ is Hydrogen, varying $-NR^2R^3$, $R^{11}$, and $R^{12}$ Similarly, following the procedures of Example 11A above, but optionally replacing 2-(4-methylphenyl)-6-chloromethylpyridine by other compounds of Formulae (33), (37), or (37a), and optionally replacing 1-(diphenylmethyl)piperazine with 1-(2,3,4-trimethoxyphenyl)piperazine or 2,2-di(4-fluorophenyl)morpholine, the following compounds of Formula (IDB) were prepared:

1-diphenylmethyl-4-[6-(4-methylphenyl)-3-methylpyridin-2-yl)methyl]piperazine dihydrochloride, m.p. 210° C.;

1-(2,3,4-trimethoxyphenylmethyl)-4-[6-(4-methylphenyl)pyridin-2-yl)methyl]piperazine dihydrochloride, m.p. 240° C.;

1-(2,3,4-trimethoxyphenylmethyl)-4-[6-(4-methylphenyl)-3-methylpyridin- 2-yl)methyl]piperazine dihydrochloride, m.p. 227° C.;

1-(2,3,4-trimethoxyphenylmethyl)-4-[6-(4-methoxyphenyl)-3-methylpyridin- 2-yl)methyl]piperazine dihydrochloride, m.p. 200° C.;

1-(2,3,4-trimethoxyphenylmethyl)-4-[6-(4-methoxyphenyl)-3-methylpyridin-N-oxide- 2-yl)methyl]piperazine dihydrochloride, m.p. 200° C.;

1-(2,3,4-trimethoxyphenylmethyl)-4-[6-(4-methoxyphenyl)-4-methylpyridin-N-oxide- 2-yl)methyl]piperazine dihydrochloride, m.p. 217° C.;

1-(2,3,4-trimethoxyphenylmethyl)-4-[6-(4-methylphenyl)pyridin-N-oxide-2-yl)methyl]piperazine dihydrochloride, m.p. 210° C.;

1-diphenylmethyl-4-[6-(4-trifluoromethylphenyl)pyridin-2-yl)methyl]piperazine dihydrochloride, m.p. 184° C.;

1-diphenylmethyl-4-[6-(4-methylphenyl)pyridin-N-oxide-2-yl)methyl]piperazine dihydrochloride, m.p. 180° C.; and 2,2-di(4-difluorophenyl)-4-[6-(4-methylphenyl)pyridin-2-yl)methyl]morpholine hydrochloride, m.p. 140° C.

EXAMPLE 12

Preparation of Compounds of Formula (ID)

A. Preparation of (IDB) where m is 0, $R^1$ is Hydrogen, $-NR^2R^3$ is 1-(Diphenylmethyl)piperazinemethyl in the 4-position, $R^{11}$ is 4-Methylphenyl, $R^{12}$ is Hydrogen, and V and U are CH A mixture of 4-formyl-2-(4-methylphenyl)pyridine (0.43 g), 1-(diphenylmethyl)piperazine (0.55 g), and titanium(IV)isopropoxide (0.75 g) was allowed to stand for 1 hour. Ethanol (2.2 ml) was added, and the resultant solution was stirred for 1 hour at room temperature. Sodium cyanoborohydride (100 mg) was then added, and the mixture stirred overnight. Water was added, the mixture filtered, and the filtrate extracted with chloroform. The organic layer was dried over anhydrous sodium sulfate, solvent evaporated off, and the residue flash-chromatographed on silica gel, eluting with 50% ethyl acetate in heptane, to yield 0.2 g of 1-diphenylmethyl-4-[2-(4-methylphenyl)-pyridin-4-yl)methyl]piperazine, which was converted to its dihydrochloride salt by treatment with anhydrous hydrochloric acid in ethanol, m.p. 220° C.

EXAMPLES 13–19

The following examples illustrate the preparation of representative pharmaceutical formulations containing an active compound of Formula (I), e.g., (±)-1-[(2,3,4-trimethoxyphenyl)- 2-methylprop-1-yl]-4-[(2-(4-trifluoromethylphenyl)- 4(5)-methyl-1H-imidazol-(5)4-yl)methyl]piperazine. Other compounds and salts of Formula (I), such as those prepared in accordance with Examples 1–12, can be used as the active compound in the formulations of Examples 13–19.

EXAMPLE 13

I.V. Formulation

| | |
|---|---|
| Active compound | 0.14 g |
| Propylene glycol | 20.0 g |
| Polyethylene glycol 400 | 20.0 g |
| Tween 80 | 1.0 g |
| 0.9% Saline solution | 100.0 ml |

Other compounds of Formula (I) and the pharmaceutically acceptable salts thereof may be substituted therein.

EXAMPLE 14

| Ingredients | Quantity per tablet, mgs. |
|---|---|
| Active compound | 25 |
| cornstarch | 20 |
| lactose, spray-dried | 153 |
| magnesium stearate | 2 |

The above ingredients are thoroughly mixed and pressed into single scored tablets.

EXAMPLE 15

| Ingredients | Quantity per capsule, mgs. |
| --- | --- |
| Active compound | 100 |
| lactose, spray-dried | 148 |
| magnesium stearate | 2 |

The above ingredients are mixed and introduced into a hard-shell gelatin capsule.

EXAMPLE 16

| Ingredients | Quantity per tablet, mgs. |
| --- | --- |
| Active compound | 1 |
| cornstarch | 50 |
| lactose | 145 |
| magnesium stearate | 5 |

The above ingredients are mixed intimately and pressed into single scored tablets.

EXAMPLE 17

| Ingredients | Quantity per capsule, mgs. |
| --- | --- |
| Active compound | 150 |
| lactose | 92 |

The above ingredients are mixed and introduced into a hard-shell gelatin capsule.

EXAMPLE 18

An injectable preparation buffered to a pH of 7 is prepared having the following composition:

| Ingredients | |
| --- | --- |
| Active compound | 0.2 g |
| $KH_2PO_4$ buffer (0.4 M solution) | 2 ml |
| KOH (1 N) | q.s. to pH 7 |
| water (distilled, sterile) | q.s. to 20 ml |

EXAMPLE 19

An oral suspension is prepared having the following composition:

| Ingredients | |
| --- | --- |
| Active compound | 0.1 g |
| fumaric acid | 0.5 g |
| sodium chloride | 2.0 g |
| methyl paraben | 0.1 g |
| granulated sugar | 25.5 g |
| sorbitol (70% solution) | 12.85 g |
| Veegum K (Vanderbilt Co.) | 1.0 g |
| flavoring | 0.035 ml |
| colorings | 0.5 mg |
| distilled water | q.s. to 100 ml |

EXAMPLE 20

Determination of $Na^+$ Channel Binding Site Affinity ($[^3H]$-batrachotoxin)

Washed rat brain synaptosomal homogenates are incubated with $[^3H]$-batrachotoxin ($[^3H]$ BTX, 5 nM) with and without the test compound over a concentration range of $10^{-10}$–$10^{-4}$M in Hepes buffer (163 mM choline, 5 mM Hepes, 1.8 mM $CaCl_2$, 0.8 mM $MgSO_4$, 0.1 mg/ml BSA, pH 7.4) containing tetrodotoxin (final assay concentration 7 μM) and scorpion toxin (final assay concentration 1 μM) in a final volume of 350 μl. Non-specific binding is defined using a saturating concentration of veratridine (0.3 mM). The assay tubes are incubated at 37° C. for 30 min then filtered over Whatman GF/B glass fibre filtermats using a Brandel cell harvester. Bound radioactivity is assessed by liquid scintillation spectrometry. The affinity of the test compounds for the $Na^+$ channel were compared as $pIC_{50}$ values.

The compounds of Formula (I) show affinity for the $Na^+$ channel.

EXAMPLE 21

Whole cell voltage clamp recordings of Sodium currents ($I_{Na}$) from N1E 115 neuroblastoma cells This is a whole cell variant of the patch clamp technique (Hammill et al., Pflugers Arch. (1981) 391, 85–100).

The ionic composition of the internal solution was (in mM): 120 CsF, 10 NaCl, 11 EGTA, 10 HEPES, 10 tetraethylammonium Cl, 1 $CaCl_2$, 1 $MgCl_2$ (pH to 7.3 with CsOH) and the external solution contained 145 NaCl, 3 KCl, 10 HEPES, 1 $CaCl_2$, 1 $MgCl_2$, 0.5 $CdCl_2$, 5 glucose (pH to 7.3 with NaOH).

Cells were held at a membrane potential of −80 mV and $I_{Na}$ was evoked by 10 ms depolarizing steps to 0 mV until a stable current was recorded. A current/voltage curve was then constructed by applying a series of depolarizing steps to membrane potentials ranging from −60 to +70 mV (increments of 10 mV). Test compounds were then applied at 3 μM or 10 μM for 10 minutes after which a second current/voltage curve was recorded.

When tested in this way, the compounds of Formula (I) produce an inhibition of the peak inward sodium current ($I_{Na}$) (measured from the current/voltage curve).

EXAMPLE 22

Whole cell voltage clamp recordings of T-type Calcium currents ($I_{Ca(T)}$)

This is a whole cell variant of the patch clamp technique (Hammill et al., Pflugers Arch. (1981) 391, 85–100).

The ionic composition of the internal solution was (in mM): 120 CsCl, 10 NaCl, 11 EGTA, 10 HEPES, 10 tetraethylammonium Cl, 1 $CaCl_2$, 1 $MgCl_2$, 40 sucrose (pH adjusted to 7.4 with CsOH) and the external solution contained 110 Tris base, 20 $BaCl_2$, 5 CsCl, 5 KCl, 20 HEPES, 30 Glucose (pH adjusted to 7.4 with HCl).

Cells were clamped at a membrane potential of −80 mV and $I_{Ca(T)}$ was evoked by 150 ms depolarizing steps to −10 mV until a stable current was elicited. A current/voltage curve was then constructed by applying a series of depolarizing steps to membrane potentials ranging from −60 to +40 mV (in increments of 10 mV). A test compound was then introduced into the superfusing medium to give a final concentration of 1 μM or 3 μM. Drug was applied for 10 minutes after which a second current/voltage curve was recorded.

When tested in this way, the compounds of Formula (I) significantly inhibit T-type calcium currents.

EXAMPLE 23

Determination of Activity Utilizing The MCA Model

Adult male mice ($CD_1$ strain), weighing 30–40 g, were anaesthetized by 5% halothane in a 70%:30% nitrous oxide:oxygen gas mixture.

The left middle cerebral artery was exposed through a curved incision midway between the eye and the external auditory meatus, the artery was sealed by thermocautery.

The dosing schedule was as follows. The first dose of test compound (0.01–0.5 mg/kg intraperitoneally) was administered 15 minutes following ischaemia. The mice then recovered for seven days, during which they were dosed with the same amount of test compound twice daily at approximately 9 am and 4 pm.

The animals were sacrificed 4 h after the last dose. The infarcted area was dissected from the ischemic left hemisphere and the contralateral right hemispherical area was also taken as control non-ischemic tissue.

Damage in the ischemic hemisphere was quantified by measuring the binding of [$^3$H] PK 11195, which provides an index of ischemic damage insofar as an increase in binding of [$^3$H] PK 11195 (assessed by $B_{max}$) indirectly reflects neuronal damage. Compounds which prevent the increase in the number of binding sites are considered to be neuroprotective.

Animals treated with placebo showed an increase in the $Bk_{max}$ of [$^3$H] PK 11195 binding in the ischemic hemisphere resulting in an increase in the ratio of binding of the left (ischemic) hemisphere:right (non-ischemic) hemisphere. This was taken as 100% damage against which the effect of test compounds could be calculated.

There were no changes in the affinity of [$^3$H] PK 11195 for its binding sites in the study.

The compounds of Formula (I) showed significant neuroprotective effects in this model.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What we claim is:

1. A compound of the formula

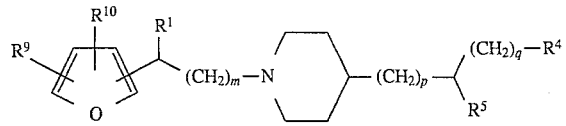

wherein
  m is 0 or 1;
  p is 0, 1, 2, or 3;
  q is 0 or 1;
  $R^1$ is hydrogen, hydroxy, or lower alkyl;
  $R^4$ is hydrogen, lower alkyl, cycloalkyl, or optionally substituted phenyl;
  $R^5$ is optionally substituted phenyl;
  $R^9$ is lower alkyl or optionally substituted phenyl; and
  $R^{10}$ is hydrogen or lower alkyl;
  with the proviso that $R^9$, $R^{10}$, and the sidechain cannot be attached to the oxygen atom;
or a pharmaceutically acceptable acid addition salt or N-oxide thereof.

2. The compound of claim 1, wherein m is 0, p is 0, q is 0, and $R^1$ is hydrogen, or a pharmaceutically acceptable acid addition salt or N-oxide thereof.

3. The compound of claim 2, wherein $R^9$ is optionally substituted phenyl and $R^{10}$ is lower alkyl, or a pharmaceutically acceptable acid addition salt or N-oxide thereof.

4. The compound of claim 3, wherein $R^4$ and $R^5$ are both phenyl, or a pharmaceutically acceptable acid addition salt or N-oxide thereof.

5. The compound of claim 4, wherein $R^9$ is 5-phenyl, $R^{10}$ is 3-methyl, and the sidechain is in the 2-position, namely 4-diphenylmethyl-1-[(5-phenyl-3-methylfuran-2-yl)methyl]piperidine, or a pharmaceutically acceptable acid addition salt or N-oxide thereof.

6. The compound of claim 4, wherein $R^9$ is 5-(4-trifluoromethyl)phenyl, $R^{10}$ is 3-methyl, and the sidechain is in the 2-position, namely 4-diphenylmethyl-1-[(5-(4-trifluoromethylphenyl)- 3-methylfuran-2-yl)methyl]piperidine, or a pharmaceutically acceptable acid addition salt or N-oxide thereof.

7. The compound of claim 3, wherein $R^4$ is 4-fluorophenyl and $R^5$ is hydrogen, or a pharmaceutically acceptable acid addition salt or N-oxide thereof.

8. The compound of claim 7, wherein $R^9$ is 5-(4-methylphenyl), $R^{10}$ is 3-methyl, and the sidechain is in the 2-position, namely 4-(4-fluorophenyl)methyl-1-[(5-(4-methylphenyl)-3-methylfuran- 2-yl)methyl]piperidine, or a pharmaceutically acceptable acid addition salt or N-oxide thereof.

9. A pharmaceutical composition comprising a therapeutically effective amount of a compound of claim 1, or a pharmaceutically acceptable acid addition salt or N-oxide thereof, in admixture with one or more pharmaceutically acceptable non-toxic carriers.

10. A pharmaceutical composition comprising a therapeutically effective amount of a compound of claim 6, or a pharmaceutically acceptable acid addition salt or N-oxide thereof, in admixture with one or more pharmaceutically acceptable non-toxic carriers.

* * * * *